(12) United States Patent
Moskowitz et al.

(10) Patent No.: US 7,972,363 B2
(45) Date of Patent: Jul. 5, 2011

(54) BI-DIRECTIONAL FIXATING/LOCKING TRANSVERTEBRAL BODY SCREW/INTERVERTEBRAL CAGE STAND-ALONE CONSTRUCTS AND POSTERIOR CERVICAL AND LUMBAR INTERARTICULATING JOINT STAPLING GUNS AND DEVICES FOR SPINAL FUSION

(76) Inventors: Ahmnon D. Moskowitz, Rockville, MD (US); Pablo A Valdivia Y Alvarado, Cambridge, MA (US); Mosheh T. Moskowitz, Rockville, MD (US); Nathan C. Moskowitz, Rockville, MD (US)

( * ) Notice: Subject to any disclaimer, the term of this patent is extended or adjusted under 35 U.S.C. 154(b) by 578 days.

(21) Appl. No.: 12/054,335

(22) Filed: Mar. 24, 2008

(65) Prior Publication Data

US 2008/0177307 A1 Jul. 24, 2008

Related U.S. Application Data

(63) Continuation-in-part of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279.

(60) Provisional application No. 60/670,231, filed on Apr. 12, 2005.

(51) Int. Cl.
*A61B 17/58* (2006.01)
(52) U.S. Cl. ........................ 606/246; 606/301; 623/17.16
(58) Field of Classification Search .................. 606/246, 606/301, 300, 144, 151, 99, 251, 266, 305; 623/17.11, 17.16; 227/181.1
See application file for complete search history.

(56) References Cited

U.S. PATENT DOCUMENTS

| | | | |
|---|---|---|---|
| 4,554,914 A | 11/1985 | Kapp et al. |
| 4,636,217 A | 1/1987 | Ogilvie et al. |
| 4,960,420 A | 10/1990 | Goble et al. |
| 4,997,432 A | 3/1991 | Keller |
| 5,123,926 A | 6/1992 | Pisharodi |
| 5,514,180 A | 5/1996 | Heggeness et al. |
| 5,660,188 A | 8/1997 | Groiso |
| 5,667,472 A | 9/1997 | Finn et al. |
| 5,782,832 A | 7/1998 | Larsen et al. |

(Continued)

OTHER PUBLICATIONS

Vincent C. Traynelis, "Prosthetics and Biologics: The Wave of the Future," Clinical Neurosurgery, vol. 50, Proceedings of the Congress of Neurological Surgeons, Philadelphia, PA 2002, Chapter 9, pp. 207-219.

(Continued)

*Primary Examiner* — Pedro Philogene
(74) *Attorney, Agent, or Firm* — Dresch IP Law, PLLC; John J. Dresch

(57) ABSTRACT

A bi-directional fixating transvertebral (BDFT) screw/cage apparatus, a posterior lumbar facet staple and a staple gun for a posterior lumbar facet staple, a posterior cervical facet joint staple, and a staple gun for a posterior cervical facet joint staple are provided. The BDFT apparatus includes an intervertebral cage including a plurality of internal angled screw guides, a plurality of screw members, and a screw locking mechanism that prevents the screw members from pulling out of the internal angled screw guides. The internal angled screw guides orient a first screw member superiorly and a second screw member inferiorly. The intervertebral cage is adapted for posterior lumbar intervertebral placement, anterior lumbar intervertebral placement, anterio-lateral thoracic intervertebral placement, or anterior cervical intervertebral placement.

42 Claims, 18 Drawing Sheets

U.S. PATENT DOCUMENTS

| | | | |
|---|---|---|---|
| 5,960,522 A | 10/1999 | Boe | |
| 6,126,689 A | 10/2000 | Brett | |
| 6,342,074 B1 * | 1/2002 | Simpson | 623/17.11 |
| 6,368,350 B1 | 4/2002 | Erickson et al. | |
| 6,375,682 B1 | 4/2002 | Fleischmann et al. | |
| 6,419,704 B1 | 7/2002 | Ferree | |
| 6,432,106 B1 * | 8/2002 | Fraser | 623/17.11 |
| 6,458,159 B1 | 10/2002 | Thalgott | |
| 6,527,804 B1 | 3/2003 | Gauchet et al. | |
| 6,533,818 B1 | 3/2003 | Weber et al. | |
| 6,558,423 B1 * | 5/2003 | Michelson | 623/17.11 |
| 6,572,653 B1 | 6/2003 | Simonson | |
| 6,579,318 B2 | 6/2003 | Varga et al. | |
| 6,582,468 B1 | 6/2003 | Gauchet | |
| 6,629,998 B1 * | 10/2003 | Lin | 623/17.11 |
| 6,641,614 B1 | 11/2003 | Wagner et al. | |
| 6,719,794 B2 | 4/2004 | Gerber et al. | |
| 6,723,126 B1 | 4/2004 | Berry | |
| 6,733,532 B1 | 5/2004 | Gauchet et al. | |
| 6,764,491 B2 | 7/2004 | Frey et al. | |
| 6,770,094 B2 | 8/2004 | Fehling et al. | |
| 6,824,564 B2 * | 11/2004 | Crozet | 623/17.11 |
| 6,904,308 B2 | 6/2005 | Frisch et al. | |
| 6,955,671 B2 | 10/2005 | Uchikubo | |
| 6,972,019 B2 * | 12/2005 | Michelson | 606/86 A |
| 7,030,904 B2 | 4/2006 | Adair et al. | |
| 7,033,394 B2 * | 4/2006 | Michelson | 623/17.11 |
| 7,037,258 B2 | 5/2006 | Chatenever et al. | |
| 7,097,615 B2 | 8/2006 | Banik et al. | |
| 7,326,248 B2 * | 2/2008 | Michelson | 623/17.11 |
| 7,442,209 B2 * | 10/2008 | Michelson | 623/17.11 |
| 2004/0088054 A1 | 5/2004 | Berry | |
| 2004/0177531 A1 | 9/2004 | DiBenedetto et al. | |
| 2004/0254644 A1 | 12/2004 | Taylor | |
| 2005/0027362 A1 | 2/2005 | Williams et al. | |
| 2005/0049590 A1 | 3/2005 | Alleyne et al. | |
| 2005/0216084 A1 | 9/2005 | Fleischmann | |
| 2005/0273170 A1 | 12/2005 | Navarro et al. | |
| 2005/0278026 A1 | 12/2005 | Gordon et al. | |

OTHER PUBLICATIONS

E.K. Wai et al., "Disk Replacement Arthroplasties: Can the Success of Hip and Knee Replacements be Repeated in the Spine?," Seminars in Spine Surgery, vol. 15, No. 4 (Dec. 2003), pp. 473-482.

Richard D. Guyer et al., "Intervertebral Disc Prostheses," Spine Journal, vol. 28, No. 15S, Supp. to Aug. 1, 2003, pp. S15-S23.

Dieter Grob et al., "Clinical Experience With the Dynesys Semirigid Fixation System for the Lumbar Spine," Spine, vol. 30, No. 3, 2005, pp. 324-331.

International Search Report (ISR) and Written Opinion of the International Searching Authority, Dec. 3, 2007, International Application No. PCT/US 07/05005.

* cited by examiner

BI-DIRECTIONAL FIXATING/LOCKING TRANSVERTEBRAL BODY SCREW/INTERVERTEBRAL CAGE STAND-ALONE CONSTRUCTS AND POSTERIOR CERVICAL AND LUMBAR INTERARTICULATING JOINT STAPLING GUNS AND DEVICES FOR SPINAL FUSION

This application is a Continuation-In-Part Application of application Ser. No. 11/842,855, filed on Aug. 21, 2007, now U.S. Pat. No. 7,942,903, which is a Continuation-In-Part of application Ser. No. 11/536,815, filed on Sep. 29, 2006, now U.S. Pat. No. 7,846,188, which is a Continuation-In-Part of application Ser. No. 11/208,644, filed on Aug. 23, 2005, now U.S. Pat. No. 7,704,279, and this application also claims priority under 35 U.S.C. §119(e) of U.S. Provisional Application No. 60/670,231, filed on Apr. 12, 2005; the entire contents of all of the above identified patent applications are hereby incorporated by reference in their entirety.

FIELD OF DISCLOSURE

The present invention relates to a unique universal bi-directional screw (BDS) system, and in particular its application to the spine, also referred to as bi-directional fixating transvertebral (BDFT) screw/cage constructs which can be used as stand-alone intervertebral devices which combine the dual functions of an intervertebral spacer that can be filled with bone fusion material(s), as well as a bi-directional transvertebral bone fixating/fusion screw apparatus. In the posterior lumbosacral and thoracic spine, intervertebral cage/BDFT screw constructs can be used as stand-alone devices obviating the need for pedicle screw fixation in many but not all cases. In the anterior cervical, thoracic and lumbosacral spine, intervertebral cage/BDFT screw constructs can be used as stand-alone devices obviating the need for anterior or lateral (thoracic) spinal plating, and/or supplemental posterior pedicle screw fixation.

The present invention also relates to percutaneous stand-alone or supplemental posterior cervical, thoracic and lumbosacral calibrated intrerarticulating joint staple guns and staples which may obviate and/or lessen the need for posterior supplemental pedicle screw fixation.

BACKGROUND

The history and evolution of instrumented spinal fusion in the entire human spine has been reviewed in related application Ser. No. 11/842,855, filed on Aug. 21, 2007, Ser. No. 11/536,815 filed on Sep. 29, 2006, and Ser. No. 11/208,644 filed on Aug. 23, 2005, the contents of which are hereby incorporated by reference in their entirety. Conventionally, the majority of posterior cervical and almost all posterior thoracic and lumbosacral fusion surgical techniques are typically supplemented with pedicle screw placement. Conventionally, the majority of anterior cervical spinal fusions, and many anterio-lateral thoracic, and anterior or anterio-lateral lumbosacral fusions are supplemented with anterior or anterior-lateral spinal plating, and very often, in particular in the thoracic and lumbosacral spine, are supplemented with posterior pedicle screw instrumentation.

Complications of pedicle screw placement in cervical, thoracic and lumbosacral spine include duration of procedure, significant tissue dissection and muscle retraction, misplaced screws with neural and/or vascular injury, excessive blood loss, need for transfusions, prolonged recovery, incomplete return to work, and excessive rigidity leading to adjacent segmental disease requiring further fusions and re-operations. Recent advances in pedicle screw fixation including minimally invasive, and stereotactic CT image-guided technology, and the development of flexible rods, imperfectly address some but not all of these issues.

Complications of anterior plating in the cervical spine include potential plate, and/or screw esophageal compression, and misplaced screws leading to neurovascular injury. Complications of anterior plating in the anterior lumbar spine include potential devastating injury to the major vessels due to chronic vascular erosion of the major vessels, or acute vascular injuries due to partial or complete plate and/or screw back out. Furthermore, for re-do surgeries, plate removal can be arduous, with potential complications of prolonged esophageal retraction, vascular injury and screw breakage. Recent advances including diminishing the plate width and/or profile, and absorbable plates, imperfectly address some but not all of these issues.

Complications of all conventional spinal anterior intervertebral device constructs are their potential for extrusion in the absence of plating. Hence, they are supplemented with anterior plating to prevent extrusion. Complications of posterior lumbosacral intervertebral device construct in the presence or absence of supplemental pedicle screw fixation is device extrusion, and potential nerve root injuries related to retraction.

SUMMARY

Herein described are multiple device embodiments which combine in a single stand-alone construct the dual functions of: a) an intervertebral cage spacer which can be filled with bone fusion material maintaining disc height, and, b) a bi-directional fixating/fusion transvertebral body screw apparatus. These embodiments are described for posterior and anterior lumbar (and anterio-lateral thoracic) intervertebral placement, and anterior cervical intervertebral placement. The present invention recognizes the aforementioned problems with prior art apparatus and solves these problems by, among other things, improving upon the designs illustrated in the aforementioned related applications. The present application provides an advanced and novel bi-directional fixating transvertebral (BDFT) screw/cage apparatus having, for example, a screw locking mechanism that prevents screw pull-out or back-out.

The exemplary embodiments of a bi-directional fixating transvertebral (BDFT) screw/cage apparatus provide as strong or stronger segmental fusion as pedicle screws without the complications arising from pedicle screw placement, which include misplacement with potential nerve and/or vascular injury, violation of healthy facets, possible pedicle destruction, blood loss, and overly rigid fusions. By placing screws across the intervertebral space from vertebral body to vertebral body, engaging anterior and middle spinal columns and not the vertebral bodies via the transpedicular route thereby excluding the posterior spinal column, then healthy facet joints, if they exist, are preserved. Because the present invention accomplishes both anterior and middle column fusion, without rigidly fixating the posterior column, the present invention in essence creates a flexible fusion.

The present invention recognizes that the very advantage of transpedicular screws which facilitate a strong solid fusion by rigidly engaging all three spinal columns is the same mechanical mechanism whereby complete inflexibility of all columns is incurred thereby leading to increasing rostral and caudal segmental stress which leads to an increased rate of re-operation.

Transvertebral fusion also leads to far less muscle retraction, blood loss and significant reduction in O.R. time. Thus, the complication of pedicle screw pull out, and hence high re-operation rate associated with the current embodiment of flexible fusion pedicle screws/rods is obviated. The lumbosacral intervertebral cage/BDFT screw constructs can be introduced via posterior lateral, transforaminal or anterior interbody fusion approaches/surgical techniques. Although one can opt to supplement these constructs with transpedicular screws there would be no absolute need for supplemental pedicle screw fixation with these operative techniques.

The anterior placement of a bi-directional fixating transvertebral (BDFT) screw/cage apparatus according to the embodiments of the present invention into the cervical and lumbar spine obviates the need for supplemental anterior cervical or anterior lumbar plating. The sole purpose of these plates is to prevent intervertebral device extrusion. This function is completely obviated and replaced by the dual functioning bi-directional fixating transvertebral (BDFT) screw/cage apparatus, according to the present invention. The obvious advantage of this is a significant savings in operative time, and prevention of injuries associated with plating, in particular esophageal, large and small vessel injuries, and spinal cord nerve root injuries.

Because the embodiments of the bi-directional fixating transvertebral (BDFT) screw/cage apparatus engage a small percentage of the rostral and caudal vertebral body surface area, multi-level fusions can be performed with these devices.

The aforementioned related applications described a novel calibrated lumbar/thoracic stapling device which staples the inferior articulating facet of the superior spinal segment to the superior articulating facet of the inferior vertebral segment unilaterally or bilaterally, which may minimize motion until interbody fusion occurs. The present invention describes evolved and improved embodiments of the previously described lumbar facet staple which enhance and strengthen its calibrated fusion. For example, an embodiment can include different strength internalized tensional springs that a surgeon may choose from for increasing strengths of fusion (decreasing levels of rigidity). Another embodiment includes a flexure spring (ratchet pawl), a much stronger calibrated ratchet which can withstand many more Newtons of applied force than that which is described in the aforementioned related applications. Furthermore, the present invention presents an evolved and improved lumbar staple gun which is far more user friendly and includes a spring return to bring the handles back to their original position after stapling, and a pull knob that opens the staple gun fingers to release a staple at will. The staple is also released automatically once it is closed. The embodiment also includes an additional feature of a return spring on the handle so that the user does not have to reset the stapler manually each time it is used. The exemplary staple gun thus makes posterior lumbar facet stapling far more amenable for percutaneous surgical stapling, and can generate via an internal spring a much stronger staple closing pressure, and a much easier staple release mechanism.

The aforementioned related applications introduced a novel posterior cervical facet stapling device which staples the inferior articulating facet of the superior cervical segment with the superior articulating facet of the inferior cervical segment either unilaterally or bilaterally. The advantage of cervical facet staples is speed and safety. The risks of cervical facet pedicle screw fixation, which include nerve root and vertebral artery injuries, are completely obviated by the use of the embodiments of the present invention. Thus, cervical facet staples achieve the same function of cervical pedicle screws without the risks.

Placement of different embodiments of the cervical facet staples which include those with two or four prongs, along unilateral and/or bilateral facet joints in a modular manner, lead to different degrees of calibrated joint motion hence introducing the novel concept of calibrated cervical fusion. In the related applications, the cervical facet staples were surgically introduced with specifically designed staple impactor tools. The present invention presents embodiments of a highly evolved cervical staple gun for the two and four pronged cervical staples. The exemplary staple gun includes a built-in trigger, trigger spring, spring hook, and return spring polyethylene cushion that improves the strength, ease and speed of staple bone penetration. Application of the cervical staple gun also makes posterior cervical facet stapling more amenable to a non-invasive, percutaneous surgical procedure. The two and four pronged staples described in the aforementioned related applications are redesigned by the present invention with a specific internalized groove to precisely fit into the cervical staple gun spring supports.

Conventionally, failed anterior lumbar arthroplasties are salvaged by combined anterior and posterior fusions. Intervertebral cage/BDFT screw constructs may be utilized as a one-step salvage mechanism for failed/extruded anteriorly placed lumbar artificial discs obviating the need for supplemental posterior pedicle screws an/or anterior lumbar plating thereby significantly reducing and/or eliminating co-morbidities associated with these other salvage procedures.

Likewise, anterior cervical intervertebral cage/BDFT screw construct placement can be used to salvage failed anterior cervical arthroplasties, and re-do fusions without having to supplement with cervical anterior plates, thereby reducing the morbidity of this procedure.

In addition, if a patient develops a discogenic problem necessitating anterior cervical discectomy and fusion at a level above or below a previously fused and plated segment, the present invention reduces or eliminates the need to remove the prior plate in order to place a new superior plate, because the function of the plate is replaced by the dual functioning intervertebral cervical construct, thereby reducing the operating room time and surgical morbidity of this procedure.

Furthermore, because of the orientation and length of the BDFT screws within the intervertebral cage/BDFT constructs, multiple level fusions can be easily performed. Posterior cervical and lumbar stapling can also be performed for multiple levels.

For example, an exemplary embodiment is directed to an intervertebral cage spacer and bi-directional fixating/fusion transvertebral body screw/cage apparatus, a posterior lumbar facet staple and a staple gun for a posterior lumbar facet staple, and a staple gun for a posterior cervical facet joint staple are provided. The apparatus includes an intervertebral cage for maintaining disc height. The intervertebral cage includes a first internal screw guide and a second internal screw guide. The apparatus further includes a first screw member having a tapered end and a threaded body disposed within the intervertebral cage, a second screw member having a tapered end and a threaded body disposed within the intervertebral cage, and a first screw locking mechanism that prevents the first screw member and the second screw from pulling-out of the first internal screw guide and the second internal screw guide.

Another exemplary embodiment is directed to an integral intervertebral cage spacer and bi-directional fixating/fusion transvertebral body screw apparatus, including an intervertebral cage having a plurality of internal angled screw guides. The apparatus further includes a plurality of screw members having a tapered end and a threaded body disposed within the plurality of internal angled screw guides of the intervertebral cage, and a screw locking mechanism that prevents the plurality of screw members from pulling out of the plurality of internal angled screw guides.

Yet another exemplary embodiment is directed to a posterior lumbar facet joint staple, including a top claw, a bottom claw, a staple pin pivotally connecting the top claw and the bottom claw, and a ratchet mechanism that limits an opening force of the top claw with respect to the bottom claw.

Another exemplary embodiment is directed to a posterior cervical facet joint staple, including a staple body having a first surface extending along a longitudinal axis. The first surface includes a plurality of prongs and a groove extending along an axis that is perpendicular to the longitudinal axis and disposed at a center point along the longitudinal axis.

Another exemplary embodiment is directed to a staple gun for a posterior lumbar facet joint staple, including a handle having a first grip and a second grip, a cylinder body having a first end for receiving the posterior lumbar facet joint staple and a second end adjacent to the handle, a connector that connects the cylinder body to the handle, and a spring return mechanism that biases the first grip and the second grip back to an original position.

Yet another exemplary embodiment is directed to a staple gun for a posterior cervical facet joint staple, including a handle, a staple guide having a first end for receiving the posterior cervical facet joint staple and a second end mounted to the handle, a plurality of supports disposed on each side of the first end of the staple guide, and for engaging the posterior cervical facet joint staple, a staple plunger disposed in the staple guide. The staple plunger has a first end for contacting the posterior cervical facet joint staple and a second end that is adjacent to the handle. The plunger is translatable between a locked position and an unlocked position. The staple gun further includes a torsional spring that applies force to the second end of the plunger along a direction of translation of the plunger from the locked position to the unlocked position, and a trigger assembly mounted to the handle for releasing the torsional spring and plunger from the locked position.

Another exemplary embodiment is directed to a method of inserting a bi-directional fixating transvertebral (BDFT) screw/cage apparatus between a first vertebral body and a second vertebral body. The method includes measuring a dimension of a disc space between the first vertebral body and the second vertebral body, determining that the disc space is a posterior lumbar disc space, an anterior lumbar disc space, or an anterior cervical disc space, selecting an intervertebral cage based on the measured dimension of the disc space and based on the determination of the disc space being the posterior lumbar disc space, the anterior lumbar disc space, or the anterior cervical disc space, inserting the selected intervertebral cage into a midline of the disc space until the selected intervertebral cage is flush or countersunk relative to the first vertebral body and the second vertebral body, inserting a first screw member into a first internal screw guide of the selected intervertebral cage, inserting a second screw member into a second internal screw guide of the selected intervertebral cage, screwing the first screw member and the second screw member into the first vertebral body and the second vertebral body respectively, confirming a position and placement of the intervertebral cage relative to the first vertebral body and the second vertebral body, and locking the first screw member and the second screw member in a final position by embedding a portion of the first screw member and the second screw member into a screw locking mechanism of the selected intervertebral cage.

BRIEF DESCRIPTION OF THE DRAWINGS

The accompanying drawings are presented to aid in the description of embodiments of the invention and are provided solely for illustration of the embodiments and not limitation thereof.

DETAILED DESCRIPTION

Aspects of the invention are disclosed in the following description and related drawings directed to specific embodiments of the invention. Alternate embodiments may be devised without departing from the scope of the invention. Additionally, well-known elements of the invention will not be described in detail or will be omitted so as not to obscure the relevant details of the invention.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

With reference to FIGS. 1A-8E, exemplary embodiments of the invention will now be described.

1. The Medical Device

Referring to FIGS. 1-3, the above described problems of the conventional art can be solved in the cervical, thoracic and lumbosacral spines by insertion into the denuded intervertebral disc space multiple embodiments of a bi-directional fixating transvertebral (BDFT) screw/cage apparatus.

Figure 1A:
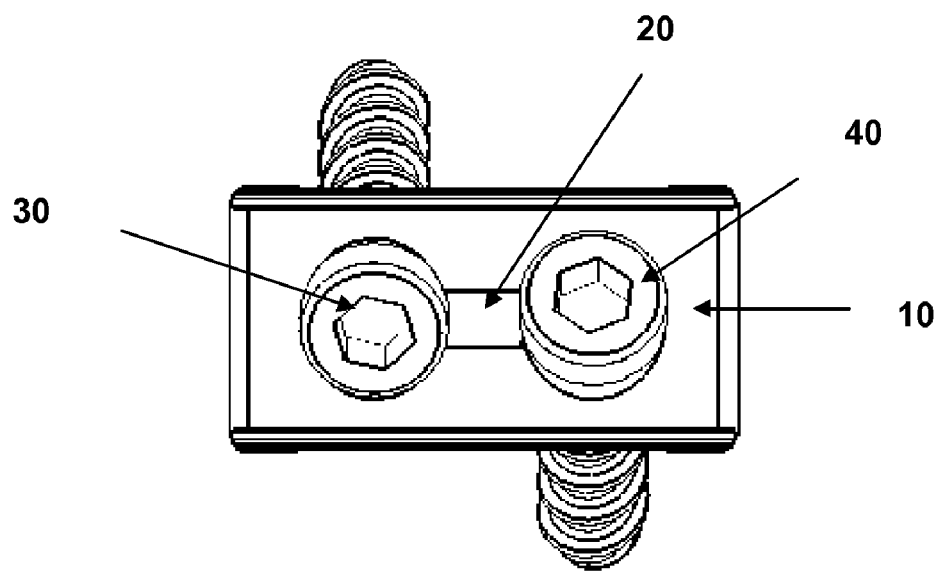
FIGS. 1A-G illustrate an embodiment of an anterior cervical intervertebral cage/BDFT screw construct in top (FIG. 1A), bottom isometric (FIG. 1B), side (FIG. 1C), isometric front (FIG. 1D), isometric bottom; partially exploded (FIG. 1E), isometric bottom; fully exploded (FIG. 1F), and isometric fully exploded with visualized internalized angled screw guides (FIG. 1G) views.
Figure 1B:
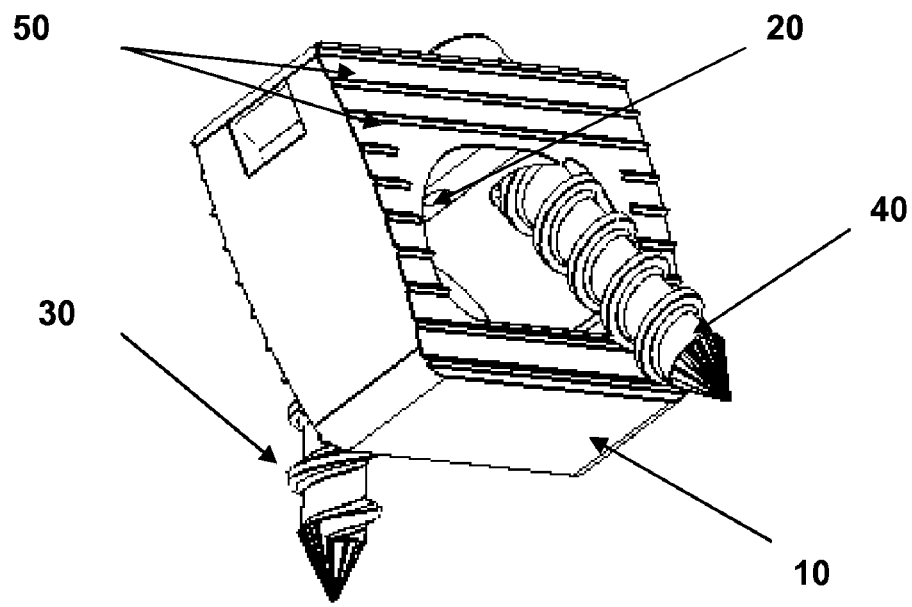
Figure 1C:
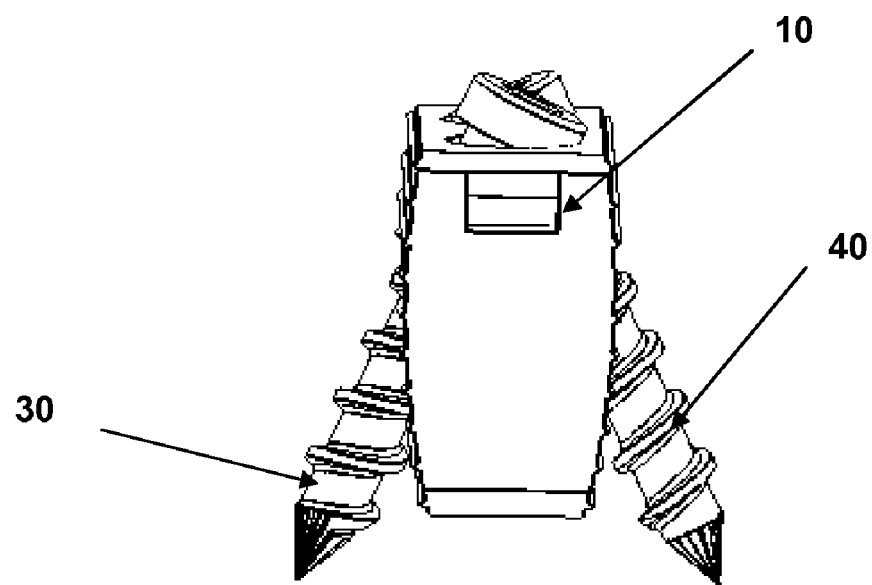
Figure 1D:
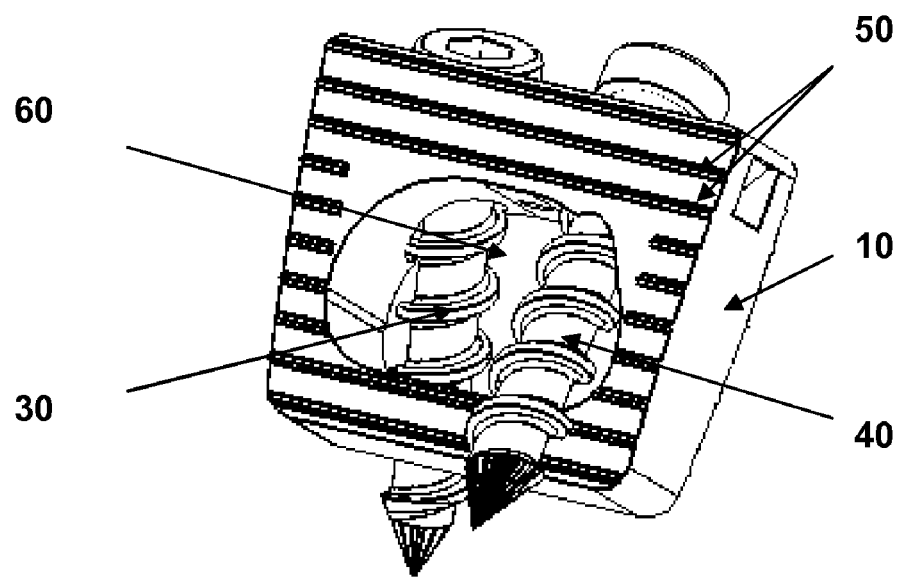
Figure 1E:
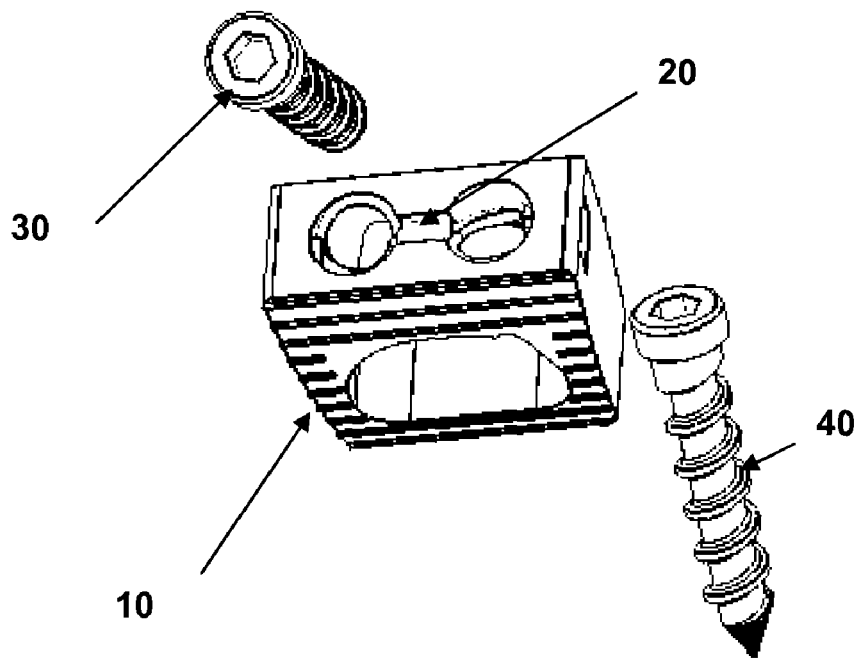
Figure 1F:
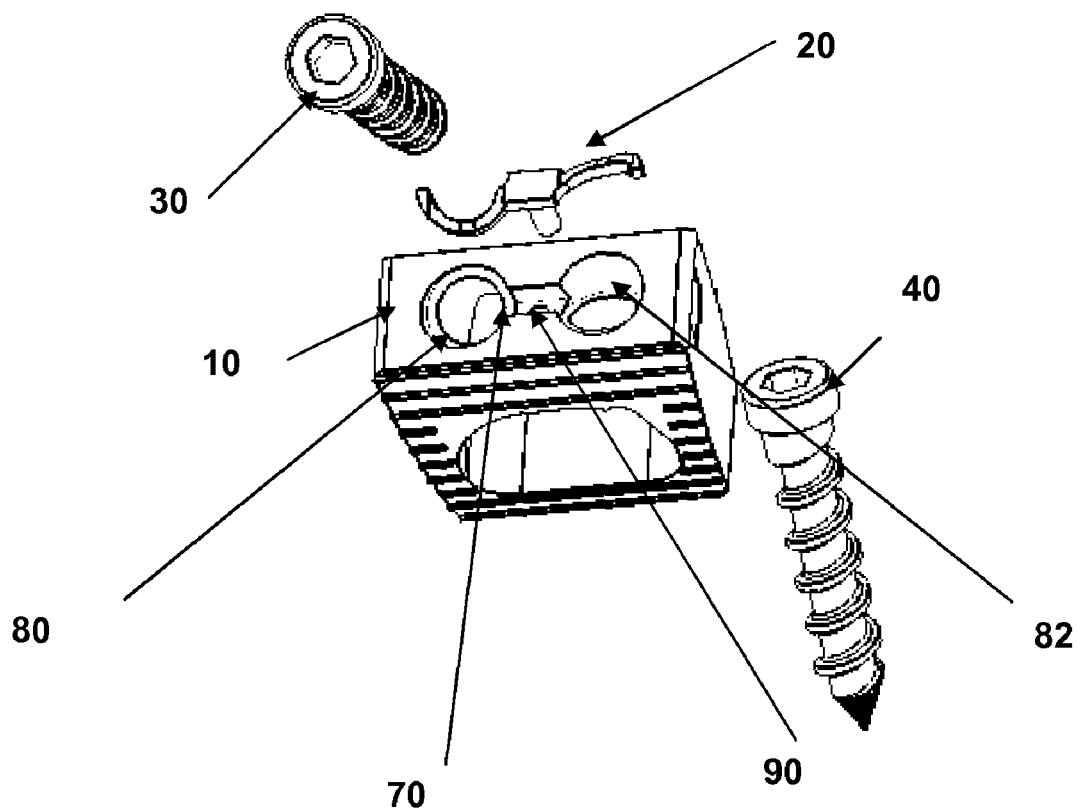
Figure 1G:
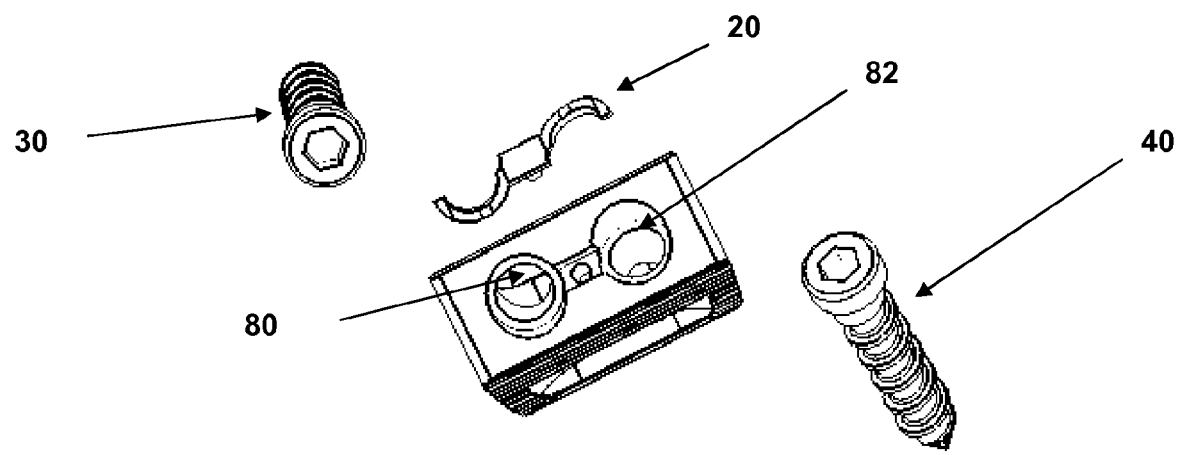

For example, FIGS. 1A-G illustrate three-dimensional views of an embodiment of an anterior cervical intervertebral cage/BDFT construct. In this embodiment, the cage 10 is elliptically contoured (FIG. 1C; side view) to fit into the bi-concave cervical disc space. The embodiment includes two screws 30, 40. A first screw 30 is oriented rostrally (superiorly) and a second screw 40 is oriented caudally (inferiorly). The cage 10 can include a cavity 60 for bone product placement. The cage 10 includes two built in internalized screw/drill guides 80, 82 (e.g., preferably having a 25 degree angulation), one for each screw 30, 40, which orient the screws 30, 40 bi-directionally in opposite directions. One of ordinary skill in the art will recognize that the internalized screw/drill guides 80, 82 can have different degrees of angulation and/or different positions within the cage 10. The built in tunnels of the screw guides 80, 82 provide an important advantage of ensuring that only one prescribed angled trajectory is possible for transvertebral screw placement. Embodiments of the intervertebral cages can be designed with internalized screw/drill guides with different angles and/or different positions within the cage. The angle and size of the screws make them amenable to single or multi-level placement. The superior and inferior surfaces or edges of the lumbar cage can include ridges 50 to facilitate integration and fusion with superior and inferior vertebral bodies. As shown in FIG. 1C, the longitudinal ends or sides of the cage 10 each include a groove or slot 15 formed therein that is adjacent to an edge of an upper surface of the intervertebral cage 10. The slot 15 can engage a screw guide of a tool, such as an insertions tool.

The embodiment also includes a screw locking mechanism 20 which can be, for example, press-fit to the top of the cage 10. The top of the cage 10 can include a perforation 90 and/or an indentation 70 for each locking mechanism 20. Each locking mechanism 20 also can be designed to rest and be press-fit into the superior surface of the in-built self drilling screw guides 80, 82. The screw locking mechanism 20 can be manufactured from a variety of materials, such as titanium. When the screws 30, 40 are turned into the screw locking mechanism 20, the screws lock by mechanically indenting the screw locking mechanism 20, thereby preventing back-out or pull-out. The locking mechanism 20 can be reused for a limited number of cycles. The locking mechanism 20 is an evolutionary advance and improvement compared to the apparatus illustrated in the aforementioned related applications. The novel embodiments of the present invention are quite unique and different from all other conventional locking mechanisms used for other types of anterior cervical plates. No other conventional anterior cervical intervertebral cage/BDFT screw constructs are known.

Figure 2A:
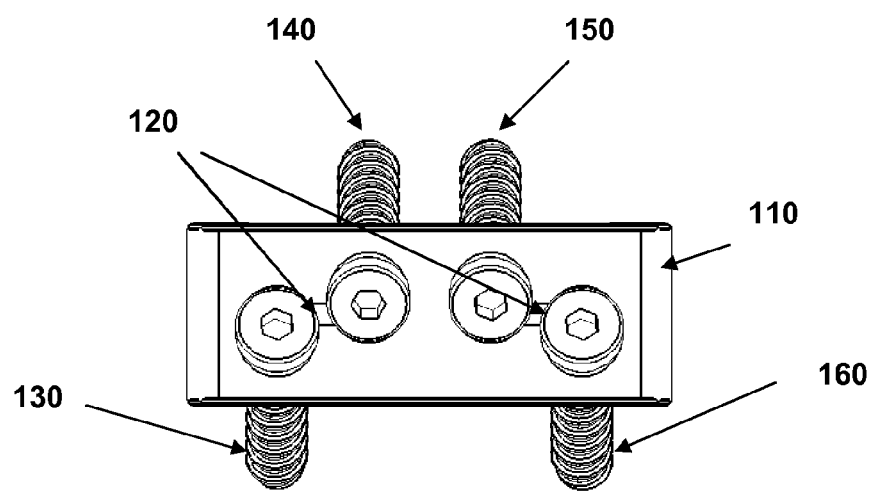
FIGS. 2A-G illustrate an embodiment of an anterior lumbar intervertebral cage/BDFT screw construct in top (FIG. 2A), bottom (FIG. 2B), front (FIG. 2C), side (FIG. 2D), isometric side (FIG. 2E), partially exploded top (FIG. 2F), and fully exploded top (FIG. 2G) views.
Figure 2B:
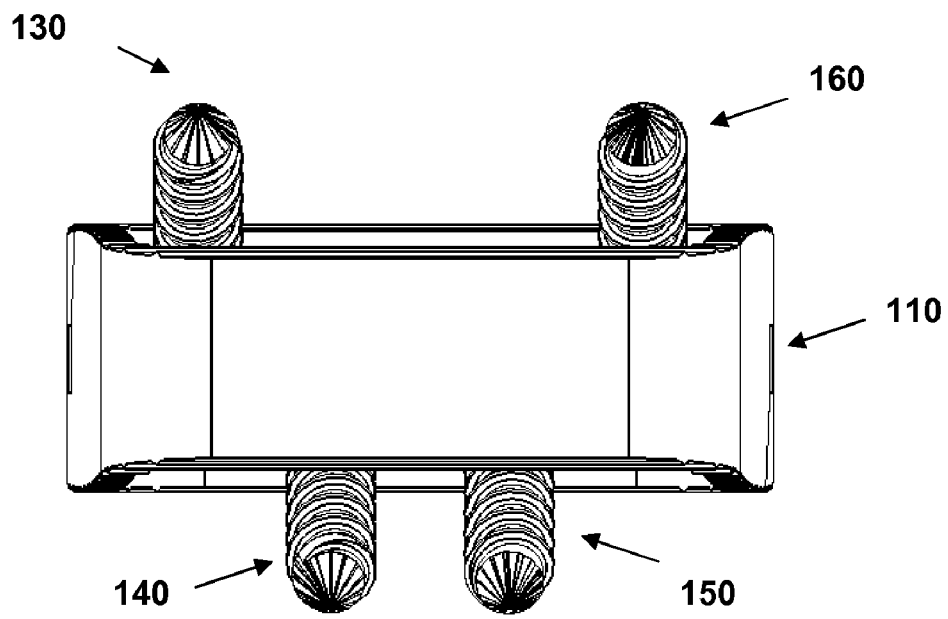
Figure 2C:
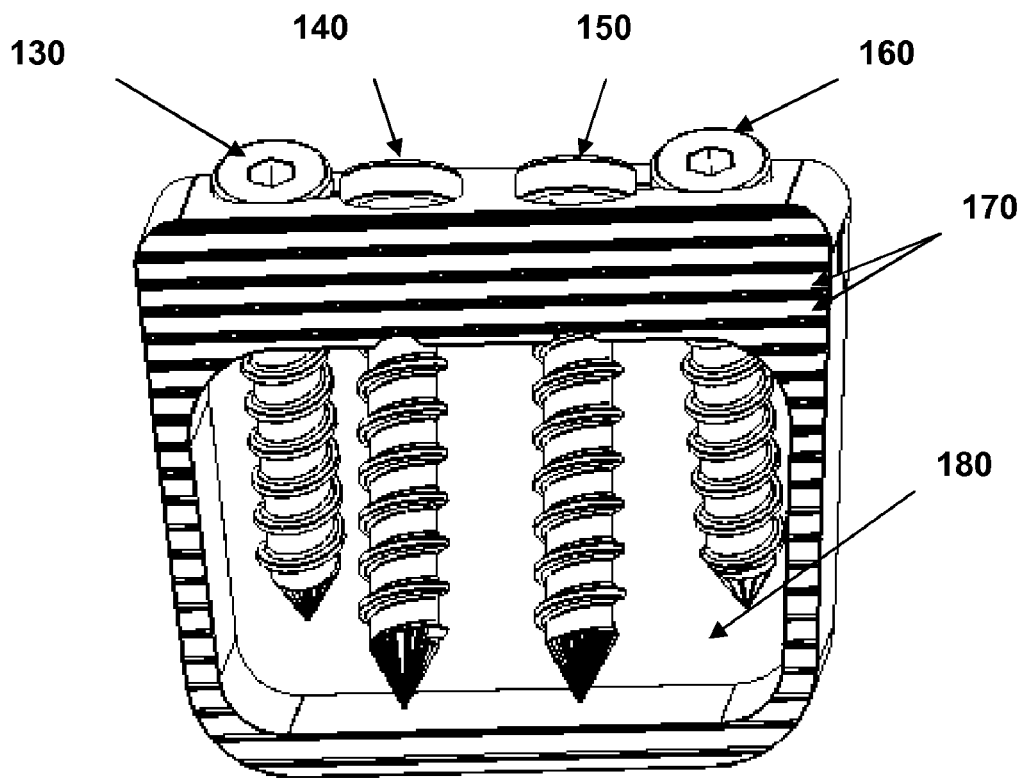
Figure 2D:
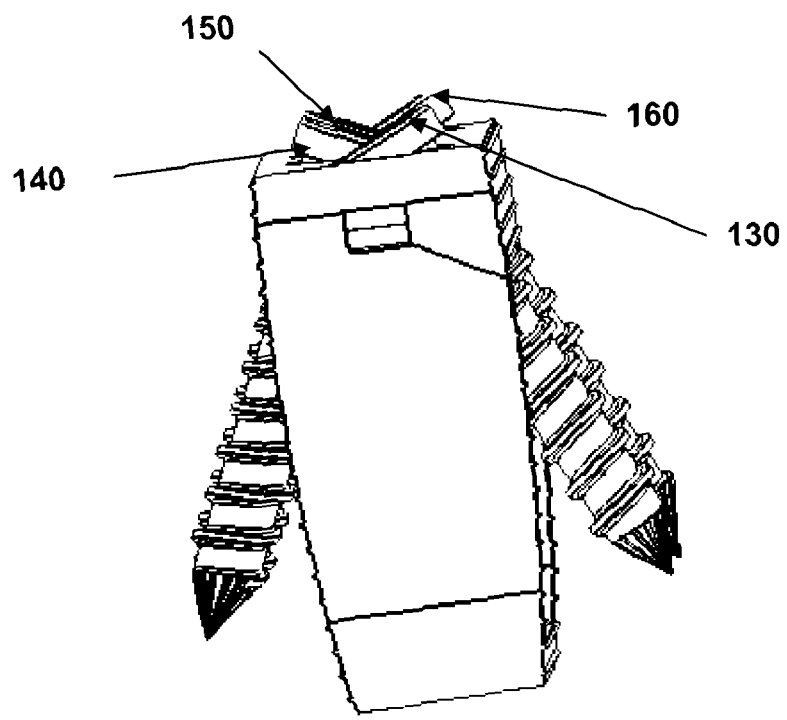
Figure 2E:
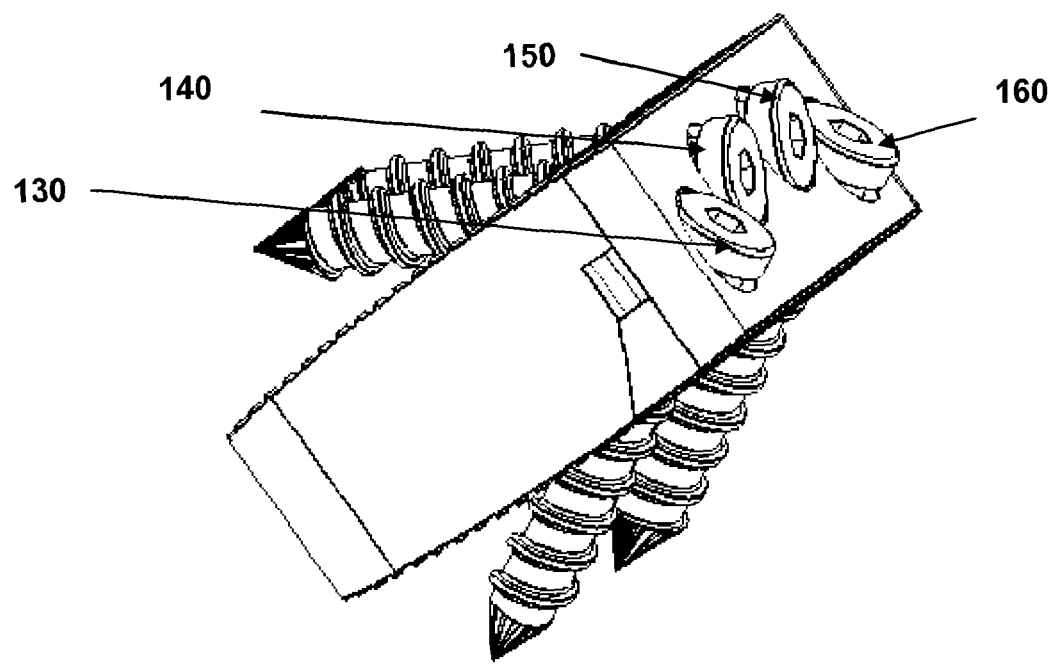
Figure 2F:
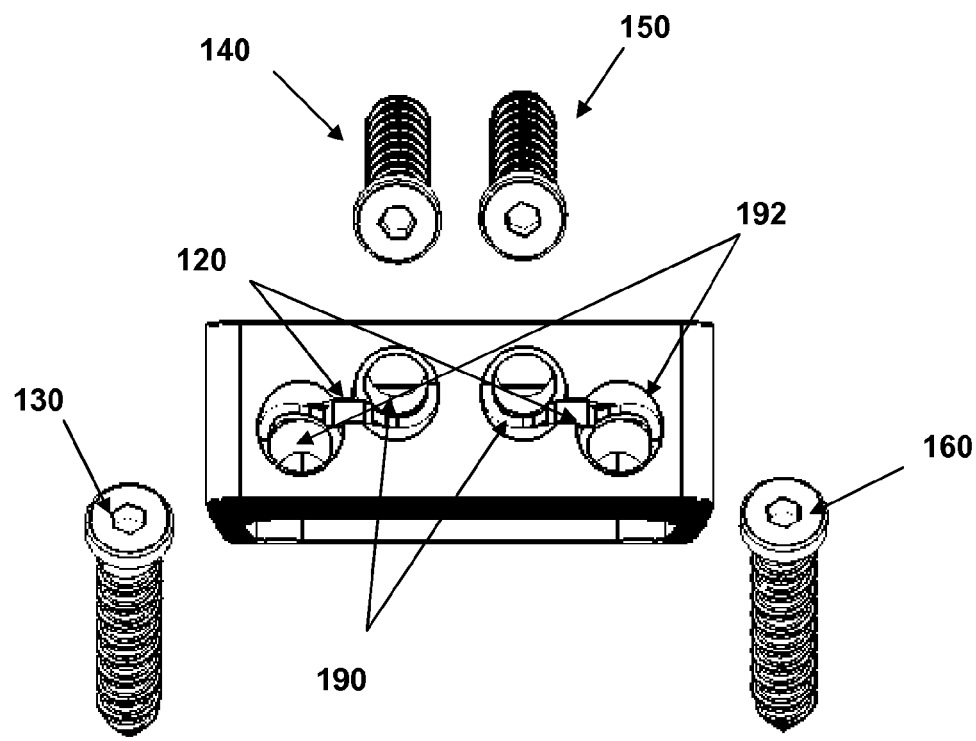
Figure 2G:
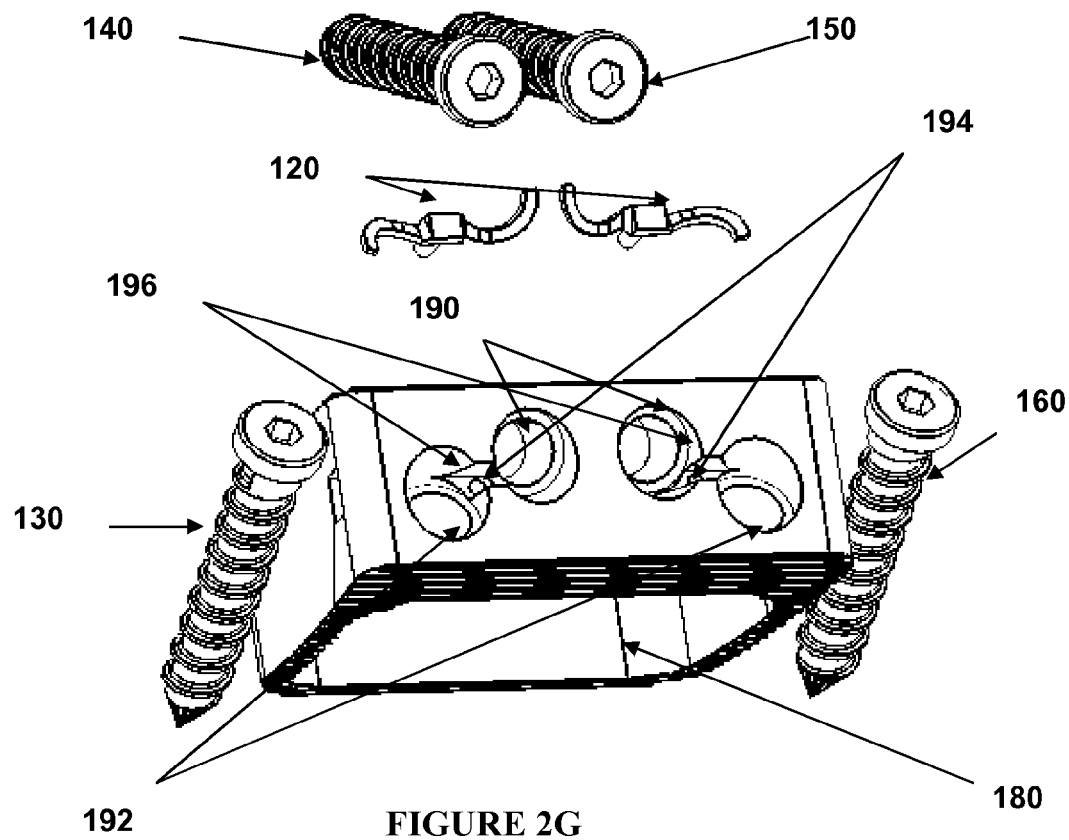

FIGS. 2A-G illustrate three-dimensional views of an embodiment of an anterior lumbar intervertebral cage/BDFT construct. In this embodiment, the cage 110 is larger than the cervical cage 10 and is also elliptically contoured to fit into the bi-concave lumbar disc space (FIG. 2D; side view). The cage 110 includes four (4) horizontally aligned internalized screw guides 190, 192 for four (4) screws 130, 140, 150, 160. The two lateral (left and right) screws are oriented inferiorly, and the two middle screws are oriented superiorly. In the embodiment, the orientations of the four screw guides 190, 192 (and screws; 130, 140, 150, 160) are selected because of their symmetry and inherent stability. The cage 110 can include a large cavity 180 for bone product placement. The cage 110 includes four built-in internalized screw/drill guides 190, 192 (e.g., having a preferred 25 degree angulation), one for each screw. Other embodiments of the intervertebral cage 110 can be designed with internalized screw/drill guides 190, 192 with different angles and/or different positions within the cage 110. The angle and size of the screws make them amenable to single or multi-level placement. The superior and inferior surfaces or edges of the cage 110 can include ridges 170 to facilitate integration and fusion with superior and inferior vertebral bodies. In an embodiment, there are no compartmental divisions in the cavity 180 for bone product placement to maximize the quantity of bone for fusion.

The cage 110 includes two screw locking mechanisms 120 that can be, for example, press-fit to the top of the cage 110. In the embodiment, there is one locking mechanism 120 per two screws. However, in other embodiments, one locking mechanism can be provided for each screw, or one locking mechanism can be provided for two or more screws. The top of the cage 110 can include a perforation 194 and/or an indentation 196 for each locking mechanism 120. Each locking mechanism 120 also can be designed to rest and be press-fit into the in-built self drilling screw guides 190, 192. The locking mechanism 120 can be manufactured from a variety of materials, such as titanium. When the screws are turned into the screw locking mechanism 120, they lock by mechanically indenting the screw locking mechanism 120. The locking mechanism 120 can be reused for a limited number of cycles. This locking mechanism 120 is an evolutionary advance and improvement compared to the apparatus illustrated in the aforementioned related applications. The novel locking mechanism 120 also is quite unique and different from all other conventional locking mechanisms used for other types of anterior lumbar cages.

Another patent which mentions anterior placed lumbar implants with perforating screws includes U.S. Pat. No. 4,904,261 (John Dove, Philip H. Hardcastle, John K. Davis and Brian King). The '261 patent discloses a horseshoe implant having a plurality of cylindrical holes with smooth inner surfaces and comprise only one stop for the heads of the bone screws to be inserted into them. The placement of five cylindrical holes is oriented within the cage in a non-symmetric manner.

In comparison, the embodiments of the present invention differ in many substantial ways from the conventional devices. For example, the present invention provides a symmetric orientation of the screw holes, as well as a screw locking mechanism. The present invention also describes an angulation/trajectory (e.g., a preferred angulation/trajectory) for preventing pull-out or back-out of the screws that would make placement of all screws in a manner which would lead to maximum stability of the construct within the vertebral space, and obviate the need for external drill guides, and surgeon trajectory angulation guess work.

In another U.S. Pat. No. 7,232,464 B2 (Claude Mathieu and Christopher Marden John Cain) multiple embodiments of lumbar intervertebral implants are presented which include one with internally threaded bore holes, another embodiment with a front plate mounted at the front surface of the implant, and another embodiment with the front place displaceably configured to move vertically relative to the implant. In addition, the disclosed preferred borehole axes are 35-55 degrees. The '464 patent has four screw perforations that are not aligned four in a row. Two of the screw holes are laterally placed on the left, one on top of each other, the top one with a superior trajectory, and the bottom with an inferior trajectory. Likewise, two perforations are placed on the right, one on top of each other, the top one with a superior trajectory and the bottom one with an inferior trajectory. The disclosed screw locking mechanism is a screw with an external thread matching the internal borehole thread, or spiral springs.

In comparison, the anterior lumbar construct of the present invention differs in many substantial ways from the conventional devices. The present invention includes a single cage construct with four (4) internalized drill guides arranged horizontally in a row. The middle two screws are oriented superiorly, and the lateral left and right screws are oriented inferiorly. This symmetric alignment of screws and orientations within the superior and inferior vertebral bodies (e.g., two middle superiorly projecting screws, and two laterally projecting inferior screws) make the fixation to the superior and inferior vertebral bodies much more symmetric and thus more stable. In an embodiment of the present invention, the cage includes a screw guide having a predetermined trajectory (e.g., a preferred trajectory of 25 degrees) that makes placement of all screws equally facile, more amenable to multi-level placement, and diminishes the need for external drill guides. Furthermore, the exemplary screw locking mechanism, which is press-fit to the cage, is unique and differs substantially from the conventional approach of matching screw/cage threads or spiral springs.

Figure 3A:
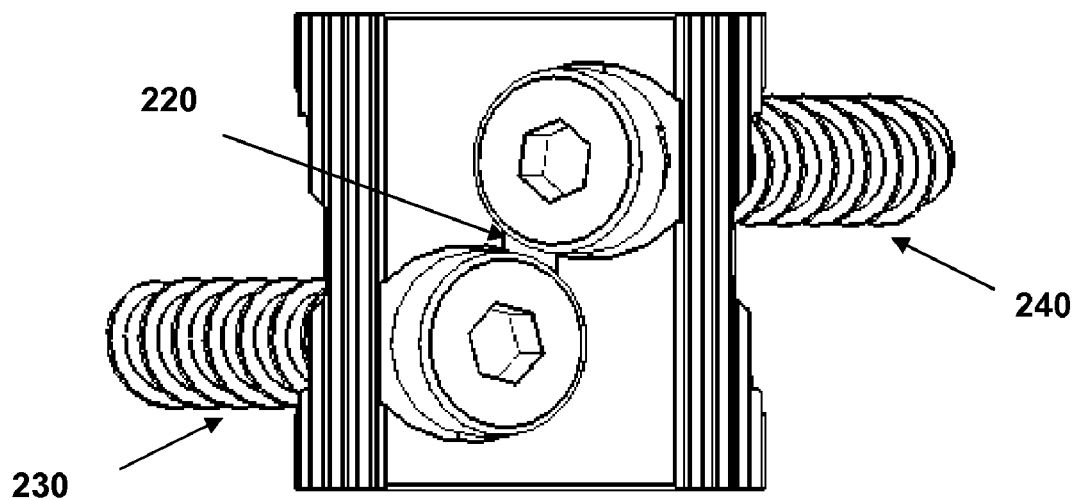
FIGS. 3A-F illustrate an embodiment of a posterior lumbar intervertebral cage/BDFT construct in top (FIG. 3A), front (FIG. 3B), side (FIG. 3C), isometric (FIG. 3D), partially exploded (FIG. 3E), and fully exploded (FIG. 3F) views.
Figure 3B:
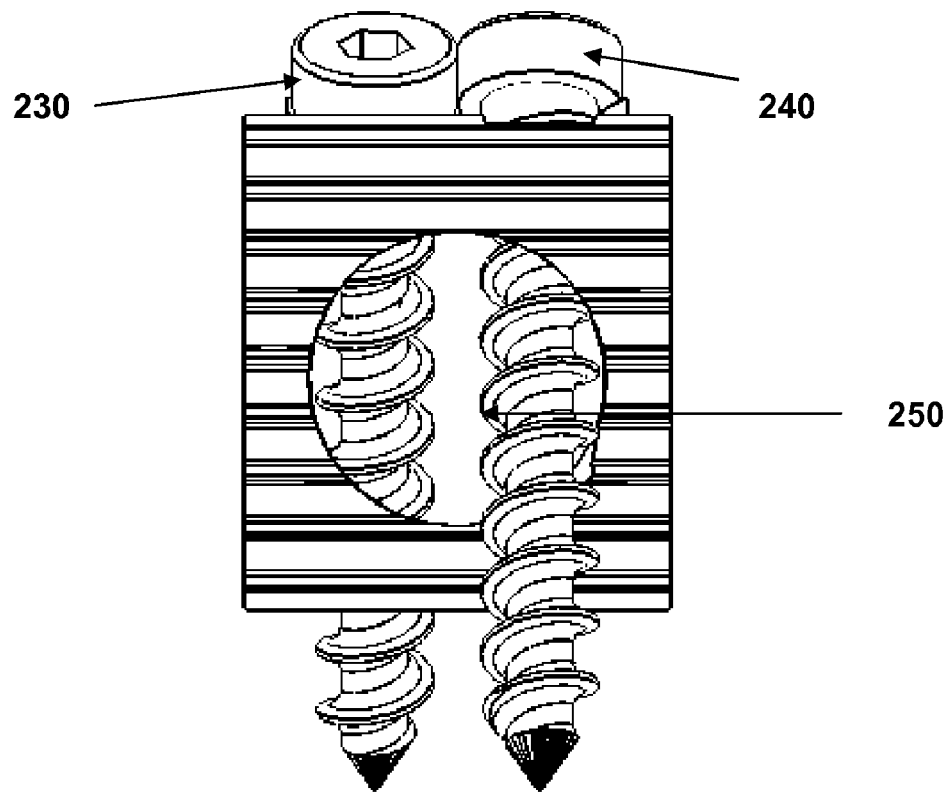
Figure 3C:
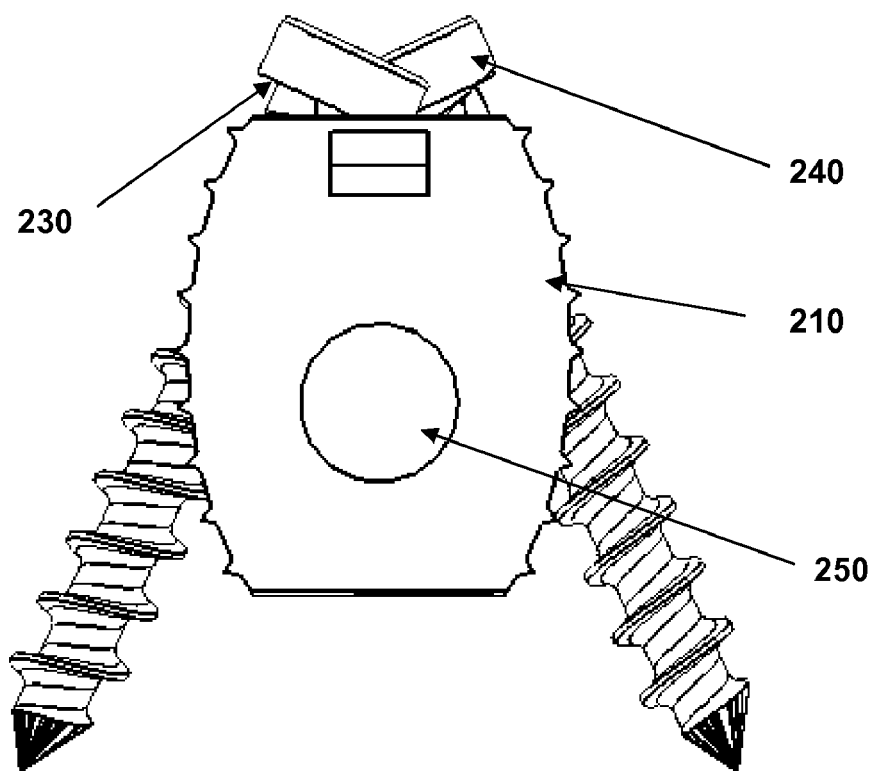
Figure 3D:
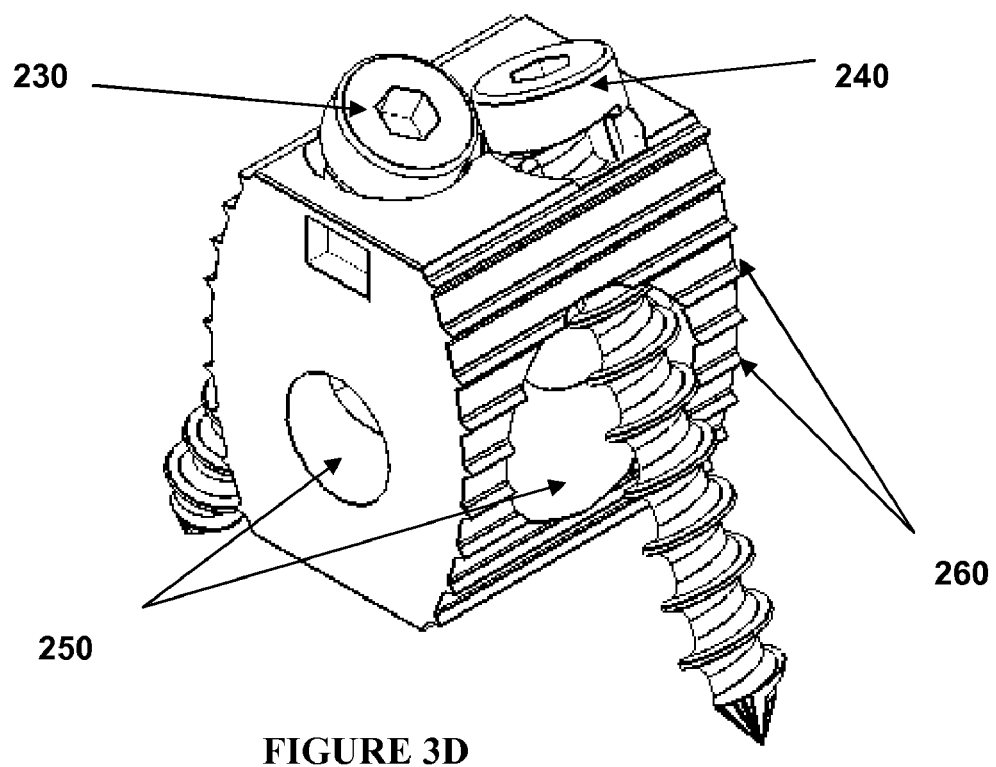
Figure 3E:
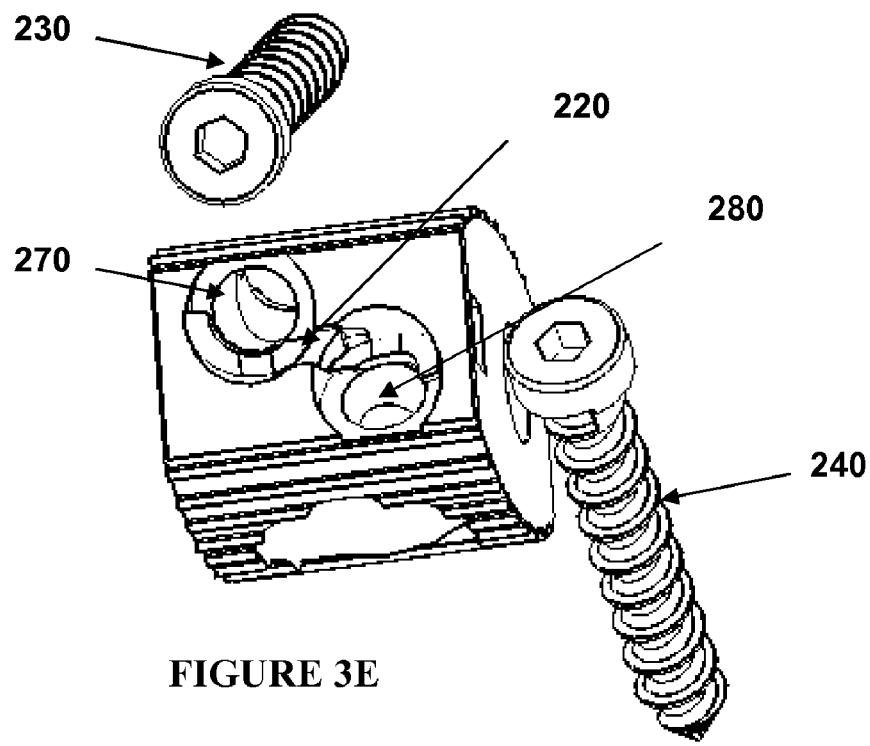
Figure 3F:
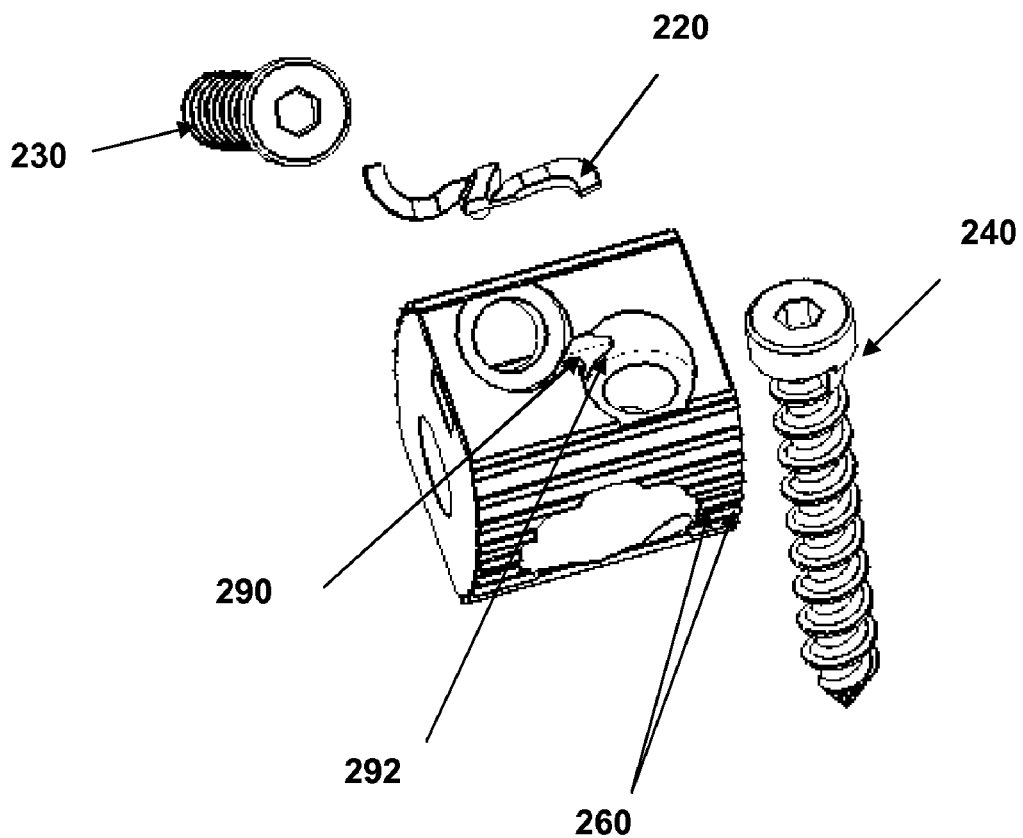

FIGS. 3A-F illustrate three-dimensional views of an embodiment of a posterior lumbar intervertebral cage/BDFT construct. In this embodiment, the screws 230, 240 perforate and orient in opposing superior and inferior directions. The cage 210 can include a cavity 250 for bone product placement. The top and bottom portions of the cage 210 are elliptically contoured to naturally fit into the bi-concave intervertebral disc space (FIG. 3C; side view). The cage 210 includes built-in internalized screw/drill guides 270, 280 having a predetermined angled trajectory (e.g., having a preferred 25 degree angulation). One of the guides is angled rostrally (superiorly) (e.g., guide 270) and the other caudally (inferiorly) (e.g., guide 280). The intervertebral cages 210 can be designed with internalized screw/drill guides 270, 280 with different angles and/or different positions within the cage 210. The angle and size of the screws 230, 240 make them amenable to single or multi-level placement. The superior and inferior surfaces or edges can include ridges 260 to facilitate integration and fusion with superior and inferior vertebral bodies. One of these constructs is placed posteriorly into the intervertebral space on the left side, and the other on the right side.

The cage 210 includes a screw locking mechanism 220 that can be, for example, press-fit to the top of the cage 210. The top of the cage 210 can have a perforation 290 and/or an indentation 292 to engage the locking mechanism 220. The locking mechanism 220 also can be designed to rest and be press-fit into the in-built self drilling screw guides 270, 280. The locking mechanism 220 can be manufactured from a variety of materials, such as titanium. When the screws 230, 240 are turned into the screw locking mechanism 220, they lock by mechanically indenting the screw locking mechanism 220. They can be reused for a limited number of cycles. The exemplary embodiment of the locking mechanism 220 is an evolutionary advance and improvement compared to the apparatus illustrated in the aforementioned related applications. The novel locking mechanism 220 also is quite unique and different from other conventional locking mechanisms used for other known cervical and lumbar anterior or posterior plate screws. No other conventional posterior lumbar intervertebral cage BDFT/screw constructs are known.

Figure 4A:
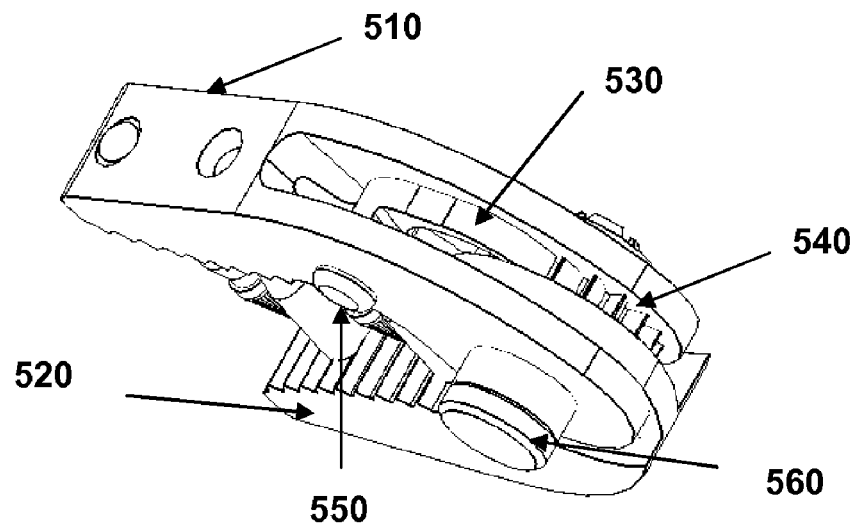
FIGS. 4A-B illustrate an embodiment of a posterior lumbar facet staple, flexure spring embodiment in side isometric (FIG. 4A) and exploded (FIG. 4B) views.
Figure 4B:
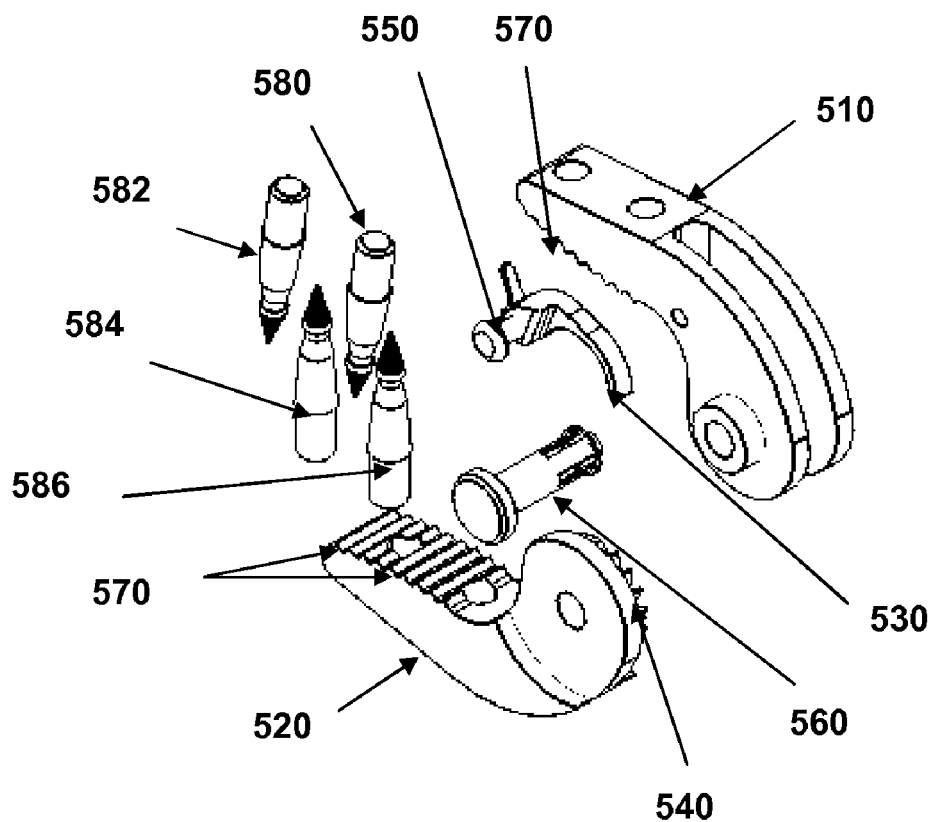
Figure 5A:
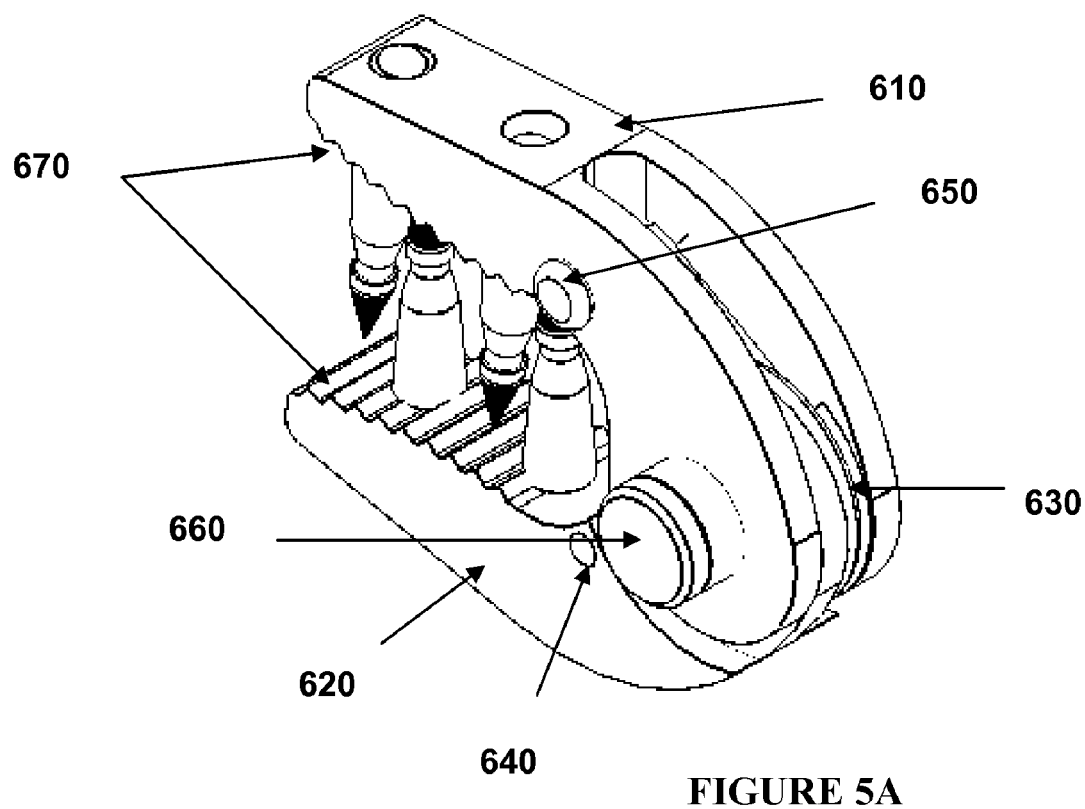
FIGS. 5A-C illustrate an embodiment of a posterior lumbar facet staple, torsional spring embodiment in side isometric (FIG. 5A), bottom isometric (FIG. 5B), and exploded (FIG. 5C) views.
Figure 5B:
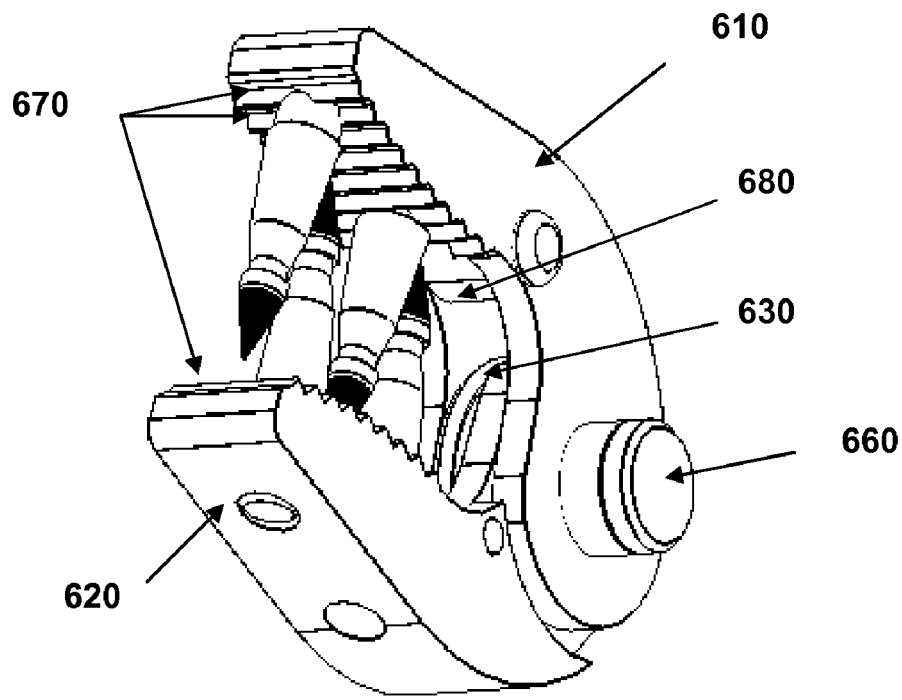
Figure 5C:
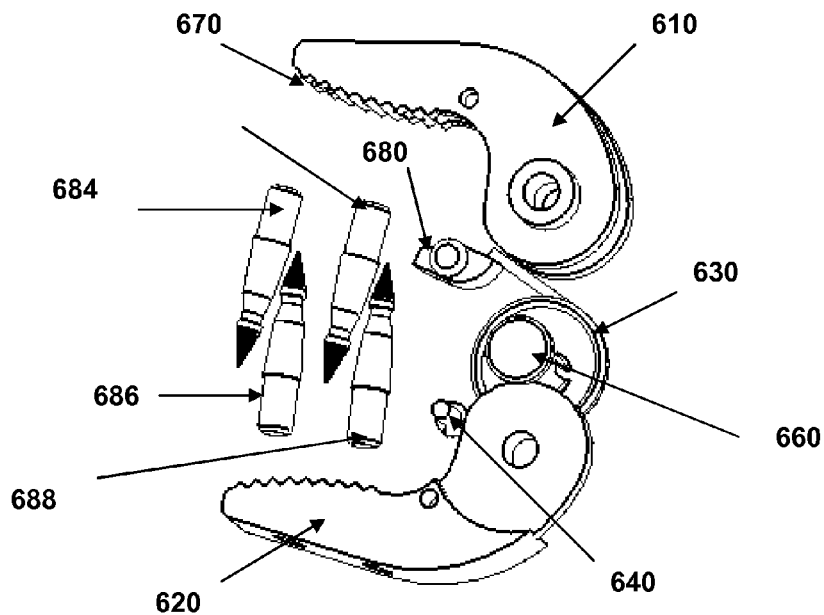

FIGS. 4A-B illustrate an embodiment of a posterior lumbar facet staple having a flexure spring. FIGS. 5A-C illustrate an embodiment of a lumbar facet staple having a torsional spring. Features of a lumbar facet staple have been thoroughly described in the aforementioned related applications, the relevant portions of which are hereby incorporated by reference herein in their entirety. The embodiments illustrated in the related applications included a ratchet. The staple could be incrementally closed with increased ratcheting over increasing number of spurs. The present invention provides two evolved embodiments, which are superior to conventional designs in that the closing mechanisms can withstand much greater force (Newtons) than a small external ratchet. Other improvements will be described below.

FIGS. 4A-B illustrate an embodiment of a posterior lumbar facet staple 500 having a flexure spring 530. As shown in FIGS. 4A-B, the features of the staple 500 include top claws 510 and bottom claws 520 with ridges 570 to help incorporate and fuse with bone. A staple pin (pivot) 560 connects the top claws 510 and bottom claws 520. The staple 500 includes four fastener pins (prongs) 580, 582, 584, 586, two per top claw 510 or bottom claw 520. Ratchet teeth 540 are molded onto the lower claw 520, and a spring loaded ratchet pawl 530 pivots on the claw, and locks the staple 500 in position. As the staple 500 closes, the ratchet 540 works in standard fashion. When a force is applied to open the staple 500, the ratchet 540 locks up, but the ratchet pawl (e.g., the flexure spring) 530 acts as a spring due to its curvature. So depending on the material used for the ratchet spring, the ratchet spring 530 can deform more or less, thereby providing different degrees of resistance. The ratchet mechanism 540 limits the opening force of the staple 500 by a force proportional to the stiffness of the flexure spring 530 (e.g., ratchet pawl). The force can be tailored by making the pawl from different materials or varying the dimension of the flexure spring on the pawl. This embodiment can achieve significant rigidity (stiffness).

FIGS. 5A-C illustrate an embodiment of a posterior lumbar facet staple 600 having a torsional spring 630. FIGS. 5A-C illustrate features of the staple 600, which include top claws 610 and bottom claws 620 with ridges 670 to help incorporate and fuse with bone. A staple pin (pivot) 660 joins the upper claw 610 and lower claw 620 of the staple 600. The staple 600 includes four fastener pins (prongs) 682, 684, 686, 688, two per top claw 610 or bottom claw 620 of the staple 600. The features of the staple 600 include a torsional spring 630, a brake 680, and a pivot spring pin 640. As the staple 600 closes, the ratchet works in standard fashion. When the staple 600 is open, the spring does not interfere with the motion. Once the staple 600 is closed there is a ratchet mechanism (brake) 680 that engages with the spring 630. At that point, the force required to open the staple 600 will depend on the stiffness of the spring 630. Having staple models with different types of springs (e.g., soft, hard, etc.) allows the tailoring of different staples to the needs of a given patient. The embodiments of the present invention have less compliance than the conventional devices.

Figure 6A:
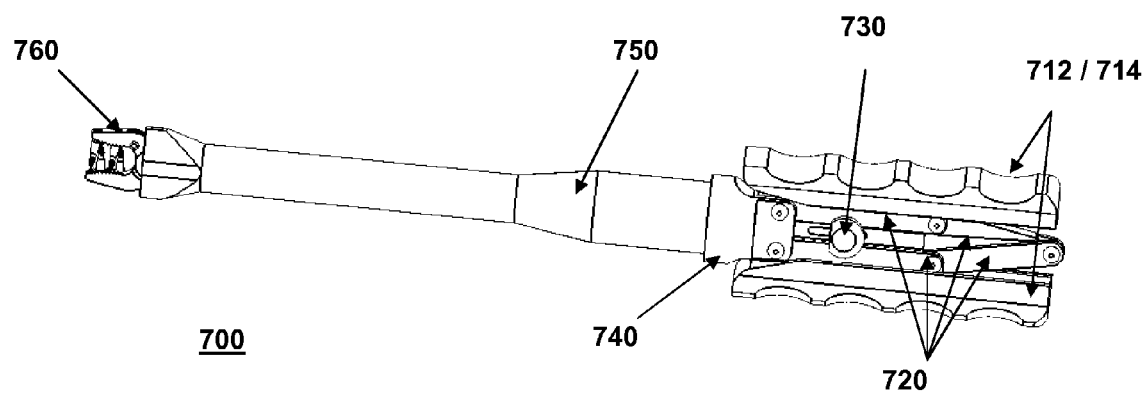
FIGS. 6A-C illustrate an embodiment of a Lumbar facet joint staple gun in side (FIG. 6A), exploded (FIG. 6B) and cross-sectional (FIG. 6C) views.
Figure 6B:
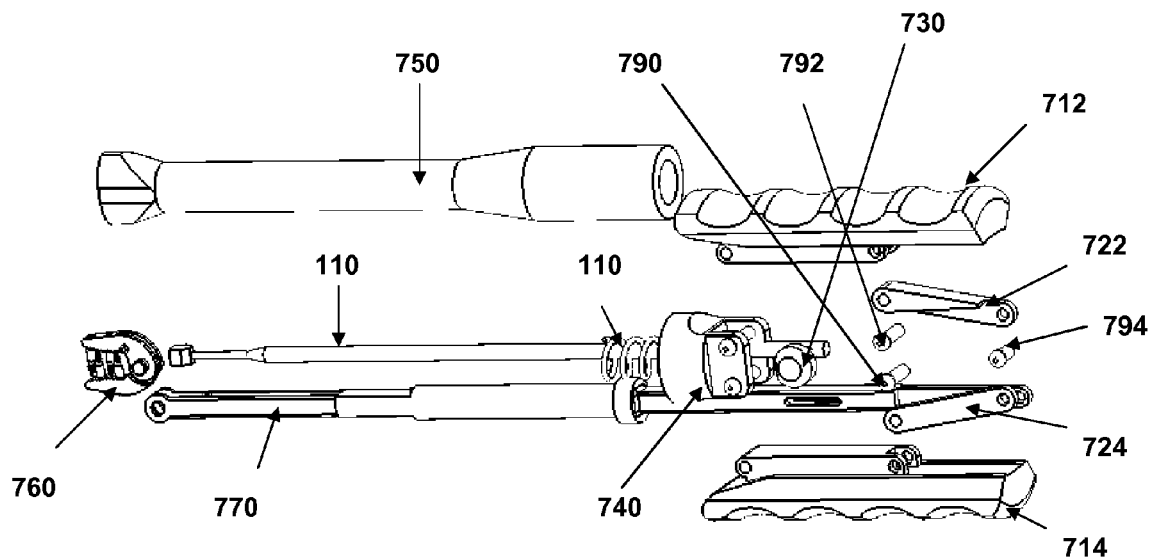
Figure 6C:
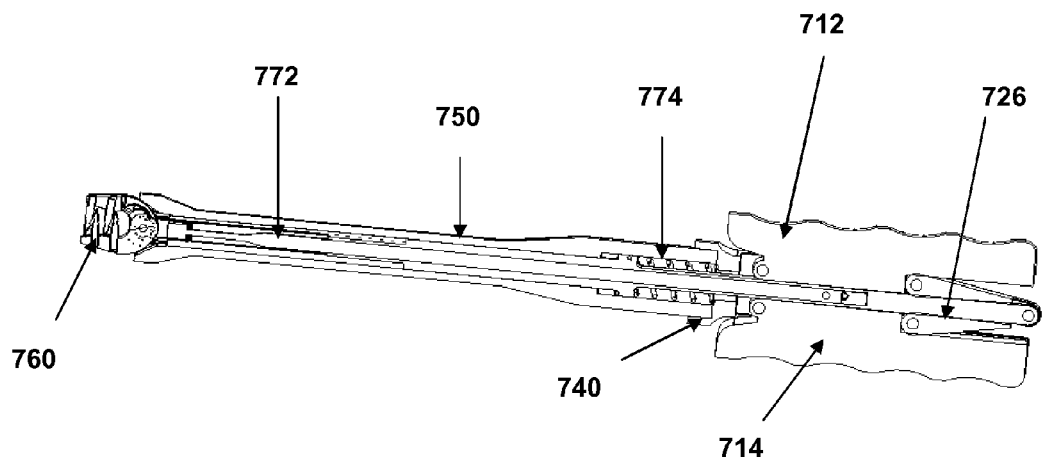

FIGS. 6A-6C illustrate an embodiment of a lumbar facet joint staple gun 700.

Features of lumbar facet joint staple guns have been thoroughly described in the aforementioned related applications, the relevant portions of which are hereby incorporated by reference in their entirety. The exemplary staple gun 700 is an evolutionary advanced version compared to the conventional designs. An improved feature of the staple gun 700 includes a spring return 274 to bring the handles (e.g., upper and lower grips 712, 714) back to their original position after stapling, and a pull knob that opens the staple fingers (e.g., claws) to release the staple 760 at will. The staple 760 in this embodiment is released automatically when it is closed. In addition, a return spring 774 is added to the handles (e.g., upper and lower grips 712, 714) so that the user does not have to reset the stapler manually each time it is used.

The figures illustrate the staple gun 700, which includes two upper and lower grips 712, 714, upper and lower bars 722, 724, a cylinder 750, an opening connector 740, an opening rod 772, an opening lever or pull knob 730, a puller 726, a connector 740, a return spring 774, and pins 790, 792, 794.

Figure 7A:
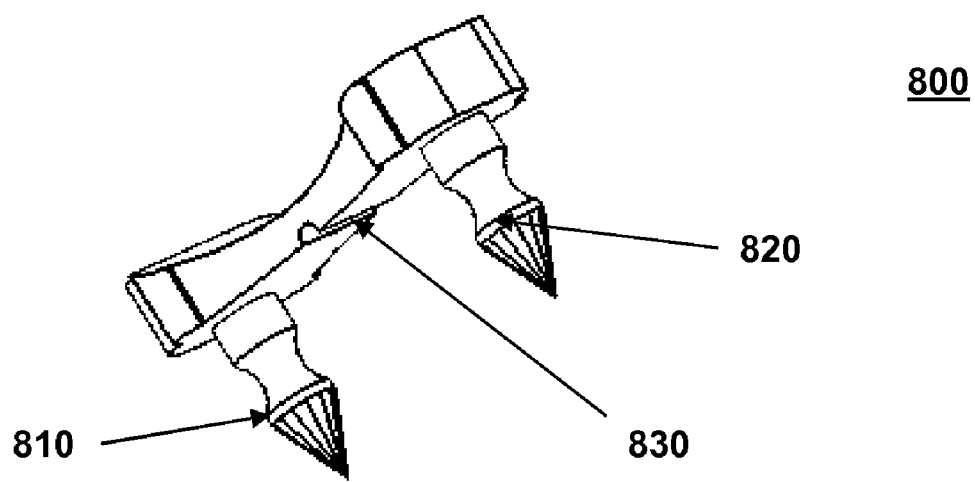
FIGS. 7A-B illustrate an embodiment of a posterior cervical facet joint staple, two pronged (FIG. 7A) and four pronged (FIG. 7B) embodiments.
Figure 7B:
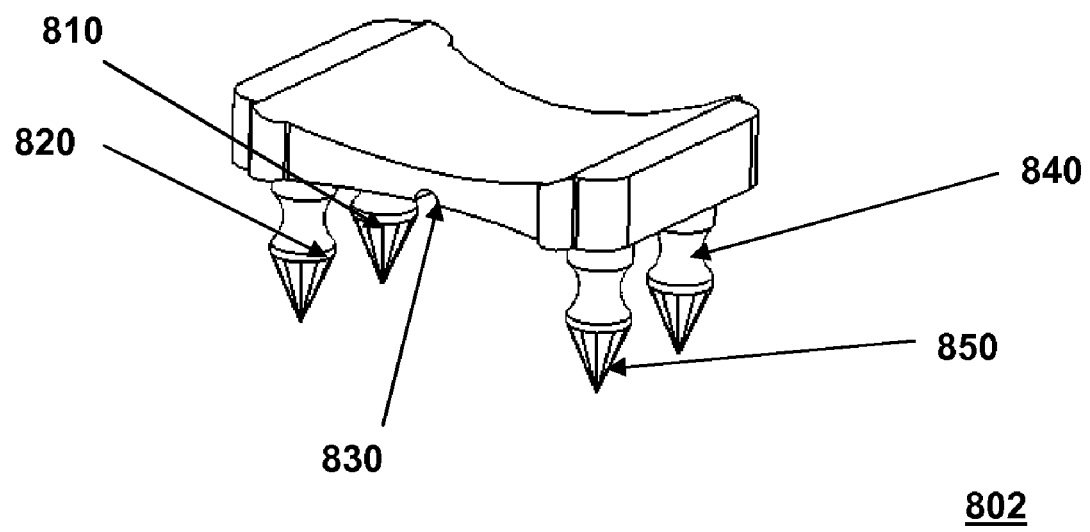
Figure 8A:
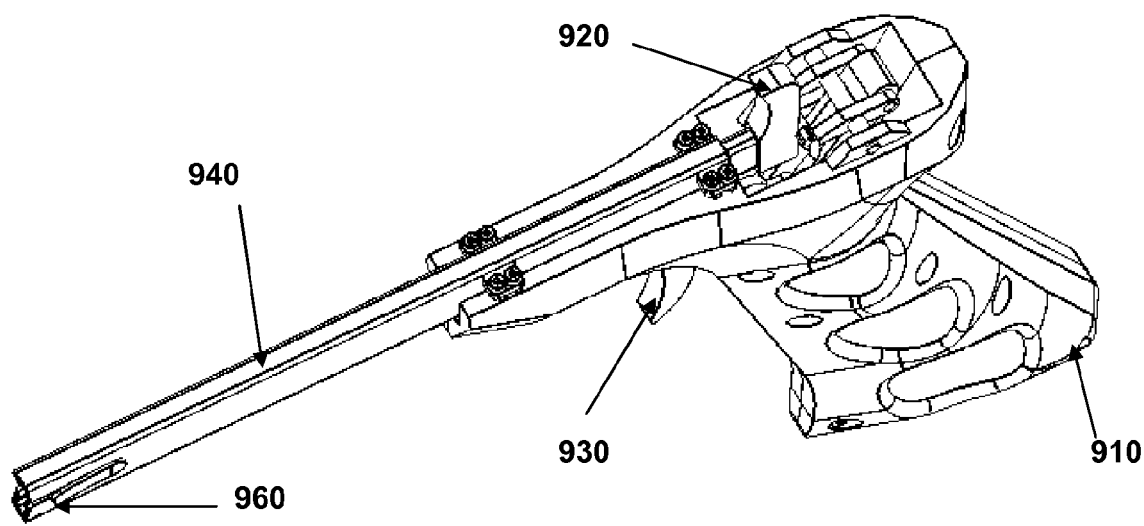
FIGS. 8A-E illustrate an embodiment of a posterior cervical facet staple gun in top-side (FIG. 8A), oblique (FIG. 8B), top (FIG. 8C), exploded (FIG. 8D), and cut-away (FIG. 8E) views.
Figure 8B:
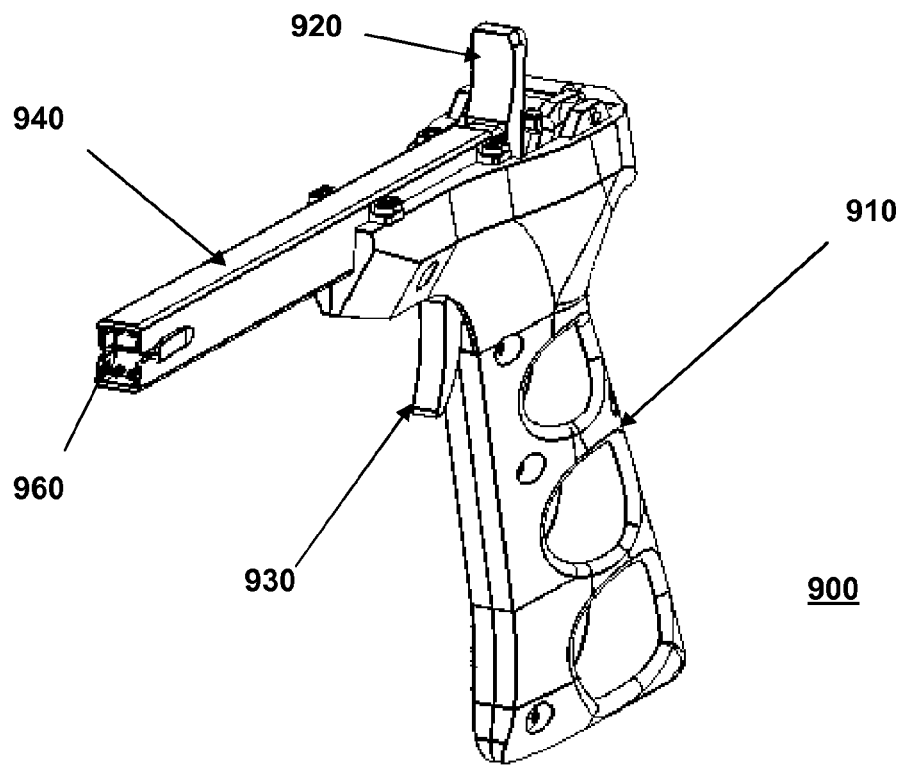
Figure 8C:
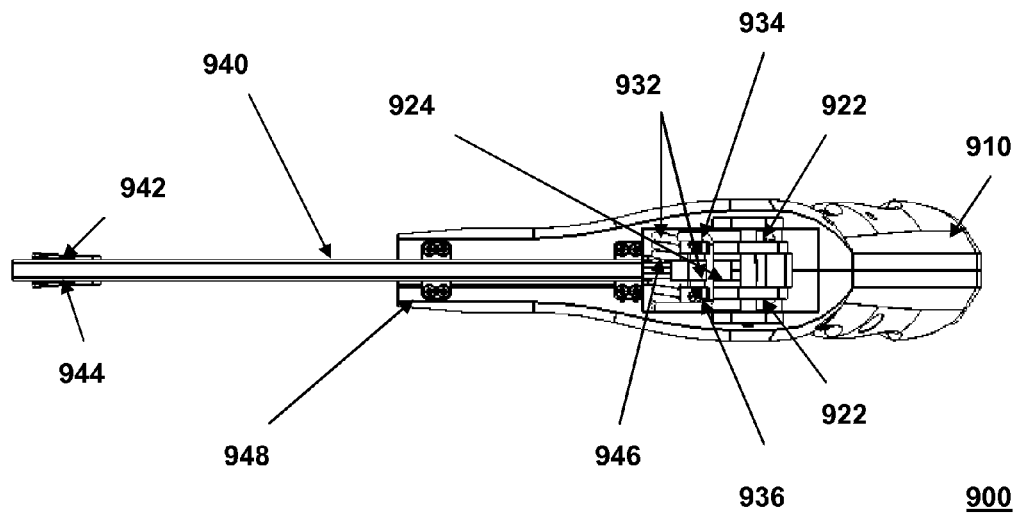
Figure 8D:
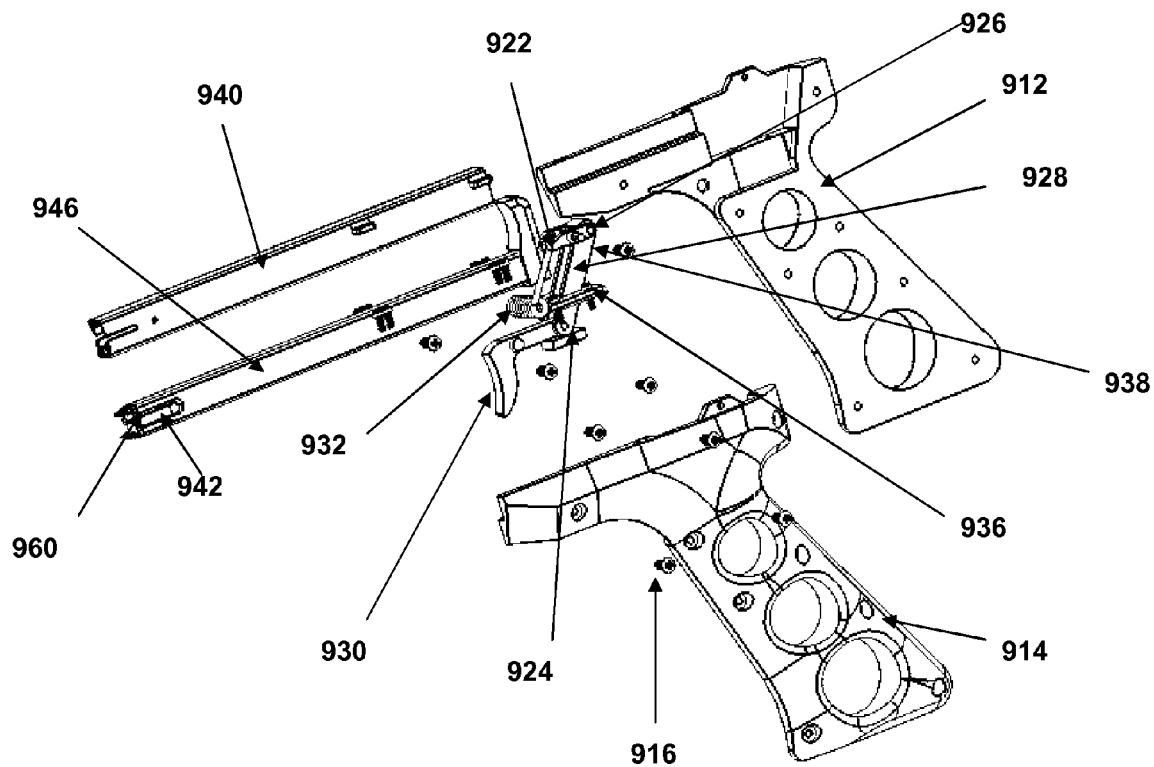
Figure 8E:
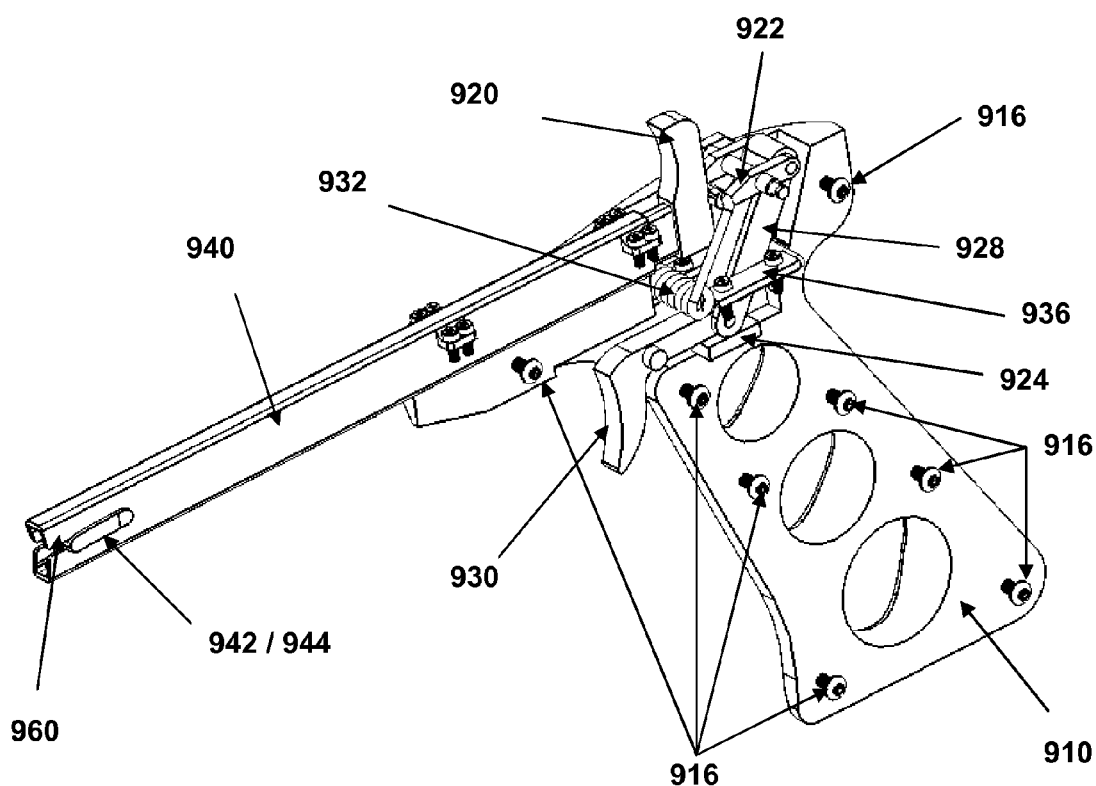

FIGS. 7A and 7B illustrate embodiments of two pronged and four pronged posterior cervical facet joint staples 800 respectively. Features of cervical facet joint staples have been thoroughly described in the aforementioned related applications, the relevant portions of which are hereby incorporated by reference in their entirety. The evolutionary advance and improvements of the present invention will now be described.

As shown in FIGS. 7A and 7B, an exemplary posterior cervical facet joint staple 800 includes a staple body extending along a longitudinal axis. The body includes a plurality of prongs (e.g., first prong 810 and second prong 820) extending from a lower surface of the staple body. The lower surface of the staple body also includes a groove 830 for engaging or fitting into the spring supports of a staple gun (e.g., a cervical staple gun, as described in more detail below). The groove 830 extends along an axis that is perpendicular to the longitudinal axis of the staple body. The groove 830 is disposed at a center point along the longitudinal axis. FIG. 7A illustrates a two-prong embodiment and FIG. 7B illustrates a four-prong embodiment.

With reference to FIGS. 8A-E, the exemplary embodiment of a staple gun 900 incorporates the staple 960 into the facet joints with much greater force than conventional methods of staple incorporation by use of a staple impactor. The speed and strength of staple placement makes the present invention more amenable to percutaneous non-invasive surgical application.

FIGS. 8A-E illustrate an embodiment of a posterior cervical facet staple gun 900.

The internal mechanism includes a handle 910 having a socket head cap screw 948, a staple guide 940, and a staple plunger 920. A staple 960 is held in place at the tip of the staple guide 940 by two spring supports 942, 944 located on each side of the tip of the guide 940. The staple plunger 920 sits behind the staple 960 and it is spring loaded by a torsional spring 932. The torsional spring 932 is compressed and held in place by a spring hook 922 connected to the staple trigger 930 via a linkage mechanism 928. When the user presses the trigger 930, the linkage mechanism 928 rotates the spring hook 922 releasing the torsional spring 932. The torsional spring 932 then pushes on the staple plunger 920 which subsequently presses on the back of the staple 960 with increasing force. The staple 960 is momentarily compressed between the plunger 920 and spring supports 942, 944 and develops enough momentum to shoot out of the guide 940 with enough force to penetrate the bone.

To reload the stapler 900, the user simply pulls on the thumb hook at the end of the plunger 920 until the spring hook 922 catches the torsional spring 932. Once the plunger 920 is locked, the user can place another staple 960 at the tip of the staple guide 940. A soft polymer (e.g., foam) pad 924 acts as a return spring for the trigger 930. One end of the torsional spring 932 is clamped to the handle 910 by a bracket (e.g., spring clamp) 936. The handle 910 is made of two symmetrical pieces 912, 914 joined by screws 916.

2. Surgical Method

Exemplary surgical steps for practicing one or more of the forgoing embodiments will now be described.

Anterior cervical spine placement of the intervertebral cage/BDFT screw construct (FIG. 1) can be implanted via previously described techniques for anterior cervical discectomy and fusion. Some but not all of these techniques include, open, microscopic, closed endoscopic or tubular. Fluoroscopic or any other form of visualized guidance can be used for this procedure.

After the adequate induction of anesthesia the patient is placed in a supine position. An incision is made overlying the intended disc space or spaces, and the anterior spine is exposed. A discectomy is performed and the endplates exposed. The disc height is measured and an anterior cervical intervertebral cage of the appropriate disc height, width and depth is selected. The central cavity is packed with bone fusion material, autologous bone graft, allograft, alone or in combination with any commercially available bone fusion promoting product. The cage is then inserted into the midline of the anterior disc space routinely until it is flush or countersunk relative to the vertebral body above and below. The BDFT screws are then inserted into the internalized rostrally (superiorly) and caudally (inferiorly) angled screw guides. A drill with or without a drill guide can be used to prepare for screw placement. This is not absolutely necessary. Because the cage has internalized screw guides, self-drilling/self-tapping screws of the appropriately selected lengths can be directly screwed into the vertebral bodies once placed into the internalized drill-guided angled tunnels. The cage's screw guides, which have internalized tunnels, direct the screws into the superior and inferior vertebral bodies in the predetermined angle of the internalized tunnels. There is no other angled trajectory other than that which is built into the internalized screw guide/tunnel of the cage that the screw can be oriented in. Hence, there is no absolute need for fluoroscopic guidance.

Once the surgeon is satisfied with the position and placement of the cage, the BDFT screws can then be locked into their final positions by the last several turns which embed them into the screw locking mechanism thereby preventing screw blackout. If the surgeon changes his mind intra-operatively or if in a future date the construct needs to be removed, the screws can be backed out. The locking mechanism has several cycles of use, and thus screws once backed out, can be re-screwed and re-locked. Multiple level placements can be performed including two, three or more levels if necessary.

Anterior or anteriolateral placement of thoracic or lumbar spine intervertebral cage/BDFT screw constructs (FIG. 2) can be implanted via previously described surgical techniques for anterior lumbar discectomy, and transthoracic, anterior-lateral thoracic discectomy. Some but not all of these techniques include, open, microscopic, closed endoscopic or tubular. Fluoroscopic or any other form of visualized guidance can be used for this procedure.

After the adequate induction of anesthesia and after the anterior spine is exposed a discectomy is performed and the endplates exposed. The disc height is measured and an anterior lumbar (or thoracic) intervertebral cage of the appropriate disc height, width and depth is selected. The central cavity is packed with bone fusion material, autologous bone graft, allograft, alone or in combination with any commercially available bone fusion promoting product. The cage is then inserted into the midline of the anterior disc space routinely until it is flush or countersunk relative to the vertebral body above and below. The four BDFT screws are then inserted into the two middle internalized rostrally (superiorly) and two lateral, caudally (inferiorly) angled screw guides. A drill with or without a drill guide can be used to prepare for screw placement. This is not absolutely necessary. Because the cage has internalized screw guides, self-drilling/self-tapping screws of the appropriately selected lengths can be directly screwed into the vertebral bodies once placed into the internalized drill-guided angled tunnels. The cage's internalized guides, which have internalized tunnels, direct the screws into the superior and inferior vertebral bodies in the predetermined angle of the internalized tunnels. There is no other angled trajectory other than that which is built into the internalized screw guide/tunnel of the cage that the screw can be oriented in. Hence there is no absolute need for fluoroscopic guidance.

Once the surgeon is satisfied with the position and placement of the cage, the BDFT screws can then be locked into their final positions by the last several turns which embed them into the screw locking mechanism thereby preventing screw blackout. If the surgeon changes his mind intra-operatively or if in a future date the construct needs to be removed, the screws can be backed out. The locking mechanism has several cycles of use, and thus screws once backed out, can be re-screwed and re-locked. Multiple level placements can be performed including two, three or more levels if necessary.

Implantation of the posterior lumbar intervertebral cage/BDFT screw constructs (FIG. 3) can be performed via previously described posterior lumbar interbody fusion (PLIF) or posterior transforaminal lumbar interbody fusion (TLIF) procedures. The procedures can be performed open, microscopic, closed tubular or endoscopic techniques. Fluoroscopic guidance can be used with any of these procedures.

After the adequate induction of anesthesia, the patient is placed in the prone position. A midline incision is made for a PLIF procedure, and one or two parallel paramedian incisions or a midline incision is made for the TLIF procedure. For the PLIF procedure, a unilateral or bilateral facet sparing hemilaminotomy is created to introduce the posterior lumbar construct into the disc space after a discectomy is performed and the space adequately prepared.

For the TLIF procedure, after unilateral or bilateral dissection and drilling of the inferior articulating surface and the medial superior articulating facet the far lateral disc space is entered and a circumferential discectomy is performed. The disc space is prepared and the endplates exposed.

The disc height is measured and a posterior lumbar intervertebral cage/BDFT screw construct (FIG. 3) of the appropriate disc height, width and depth is selected. The central cavity is packed with bone fusion material, autologous bone graft, allograft, alone or in combination with any commercially available bone fusion promoting product. Then one construct is placed on either right or left sides, or one construct each is placed into left and right sides. The constructs are inserted such they are flush or countersunk relative to the superior and inferior vertebral bodies. In addition to the central cavities that are packed with bone product, the intervertebral space in between the constructs can also be packed with bone product for fusion.

The BDFT screws are then inserted into internalized rostrally (superiorly) and caudally (inferiorly) angled screw guides. A drill with or without a drill guide can be used to prepare for screw placement. This is not absolutely necessary. Because the cage has internalized screw guides, self-drilling/self-tapping screws of the appropriately selected lengths can be directly screwed into the vertebral bodies once placed into the internalized drill-guided angled tunnels. The cage's internalized guides, which have internalized tunnels, direct the screws into the superior and inferior vertebral bodies in the predetermined angle of the internalized tunnels. There is no other angled trajectory other than that which is built into the internalized screw guide/tunnel of the cage that the screw can be oriented in. Hence, unlike posterior placement of pedicle screws there is no absolute need for fluoroscopic or expensive and cumbersome, frameless stereotactic CT guidance.

Once the surgeon is satisfied with the position and placement of the cage(s), the BDFT screws can then be locked into their final positions by the last several turns which embed them into the screw locking mechanism thereby preventing screw backout. If the surgeon changes his mind intra-operatively or if in a future date the construct needs to be removed, the screws can be backed out. The locking mechanism has several cycles of use, and thus screws once backed out, can be re-screwed and re-locked. Multiple level placements can be performed including two, three or more levels.

The surgical placement of the lumbar facet staples (FIGS. 4 and 5) via a posterior facet lumbar staple gun (FIG. 6) is described in the aforementioned related applications. The surgical procedure for these staple embodiments with this staple gun embodiment is identical to that which has been previously described. The evolutionary advantages of these embodiments are explained above.

For posterior placement of the cervical facet staples (FIG. 7) using the cervical facet staple gun (FIG. 8), after the adequate induction of anesthesia the patient is flipped prone and his head and neck secured. A single midline or two paramedian incisions are made for unilateral or bilateral or multilevel placement of cervical staples. Ultimately the facet joint is exposed. Alternatively and preferably this can be performed percutaneously under fluoroscopic guidance with IV sedation. The cervical staple, two or four pronged is loaded either into the two or four pronged staple gun, is placed on the two articulating cervical facets, and then stapled into the joint using the staple gun. To achieve modular calibrated fusion, different combinations and permutations of cervical facet staples can be inserted ranging from a single unilateral two pronged staple providing a high degree of flexibility to a total of four bilaterally placed four pronged cervical staples leading to the highest degree of rigidity per cervical posterior joint. Additional bone may or may not be placed in the vicinity to facilitate permanent and solid fusion. This evolved cervical staple gun compared to our prior staple impactor makes this procedure more amenable to percutaneous, and more precise staple placement, as well as more contoured staple-bone integration.

The present inventions may provide effective and safe techniques that overcome the problems associated with current transpedicular based cervical, thoracic and lumbar fusion technology, as well as anterior cervical, thoracic and lumbar plating technology, and for many degenerative stable and unstable spinal diseases. These inventions could replace much pedicle screw, and anterior plating based instrumentation in many but not all degenerative spine conditions.

The speed and simplicity of placement of posterior cervical and lumbar facet staples, placement of anterior and posterior lumbar intervertebral cage/BDFT screw constructs, and placement of anterior cervical cage/BDFT screw constructs far exceeds that of current pedicle screw and anterior spinal plating technology. Furthermore, these devices have markedly significantly decreased risk of misguided screw placement and hence decreased risk of neurovascular injury, and blood loss. In the cervical and lumbar spines, intervertebral cage/BDFT screw constructs and facet staples could be applied modularly in different combinations to achieve different degrees of rigidity (flexibility). Furthermore, the posterior cervical and lumbar staple technology is amenable to short same-day procedures performed under local IV anesthesia with a rapid recovery time. The lumbar and cervical intervertebral cage/BDFT screw constructs all would have decreased recovery time, and more rapid return to work time compared to pedicle screw, and plating technology. These devices with great probability lead to similar if not equal fusion rates, with substantially less morbidity, and hence, overall, make them a major advance in the evolution of spinal instrumented technology leading to advances in the compassionate care of the spinal patient.

While the foregoing disclosure shows illustrative embodiments of the invention, it should be noted that various changes and modifications could be made herein without departing from the scope of the invention as defined by the appended claims. The functions, steps and/or actions of the method claims in accordance with the embodiments of the invention described herein need not be performed in any particular order. Furthermore, although elements of the invention may be described or claimed in the singular, the plural is contemplated unless limitation to the singular is explicitly stated.

What is claimed is:

1. A bi-directional fixating transvertebral (BDFT) screw/cage apparatus, comprising:
   an intervertebral cage for maintaining disc height, the intervertebral cage including a first internal screw guide and a second internal screw guide;
   a first screw member having a screw head, a tapered end, and a threaded body disposed within the intervertebral cage;
   a second screw member having a screw head, a tapered end, and a threaded body disposed within the intervertebral cage; and
   a first screw locking mechanism that prevents the first screw member and/or the second screw from pulling-out of the first internal screw guide and the second internal screw guide,
   wherein the first screw locking mechanism is disposed between the intervertebral cage and an underside of the screw head of the first screw member and/or the second screw member when the first screw locking mechanism is in a locked state.

2. The apparatus according to claim 1, wherein each of the first internal screw guide and the second internal screw guide is angled to orient the first screw member and the second screw bi-directionally in opposite directions.

3. The apparatus according to claim 2, wherein the first screw member is oriented rostrally (superiorly) and the second screw member is oriented caudally (inferiorly).

4. The apparatus according to claim 1, wherein the first internal screw guide and the second internal screw guide are aligned along a longitudinal axis of the intervertebral cage.

5. The apparatus according to claim 1, wherein the first internal screw guide and the second internal screw guide are symmetrically disposed on each side of a center point of the intervertebral cage along a longitudinal axis of the intervertebral cage.

6. The apparatus according to claim 1, wherein each of the first internal screw guide and the second internal screw guide includes a tunnel that permits only a predetermined angled trajectory of the first screw member and the second screw member.

7. The apparatus according to claim 1, wherein a predetermined angled trajectory of the first internal screw guide is different than a predetermined angled trajectory of the second internal screw guide.

8. The apparatus according to claim 1, wherein the first screw locking mechanism is press-fit into a surface of the intervertebral cage.

9. The apparatus according to claim 1, wherein the intervertebral cage includes an indentation and/or perforation that receives the first screw locking mechanism to secure the first locking mechanism to the intervertebral cage.

10. The apparatus according to claim 1, wherein the first screw locking mechanism is press-fit into the first internal screw guide and/or the second internal screw guide to secure the first locking mechanism to the intervertebral cage.

11. The apparatus according to claim 1, wherein an exterior surface of the intervertebral cage includes a plurality of ridges.

12. The apparatus according to claim 11, wherein the plurality of ridges are disposed on a superior surface and/or an inferior surface of the intervertebral cage.

13. The apparatus according to claim 1, wherein the intervertebral cage includes at least one cavity for receiving bone fusion material.

14. The apparatus according to claim 1, wherein the intervertebral cage is an elliptically contoured cervical intervertebral cage adapted to fit into a bi-concave cervical disc space.

15. The apparatus according to claim 1, wherein the intervertebral cage is an elliptically contoured lumbar intervertebral cage adapted to fit into a bi-concave lumbar disc space.

16. The apparatus according to claim 1, wherein the intervertebral cage is an elliptically contoured posterior lumbar intervertebral cage adapted to fit into a bi-concave lumbar disc space.

17. The apparatus according to claim 1, wherein the intervertebral cage is configured for one of posterior lumbar intervertebral placement, anterior lumbar intervertebral placement, anterio-lateral thoracic intervertebral placement, and anterior cervical intervertebral placement.

18. The apparatus according to claim 1, further comprising:
   a third screw member having a tapered end and a threaded body disposed within the intervertebral cage; and
   a fourth screw member having a tapered end and a threaded body disposed within the intervertebral cage,
   wherein the intervertebral cage includes:
   a third internal screw guide and a fourth internal screw guide; and
   a second screw locking mechanism that prevents the third screw member from pulling out of the third internal screw guide and the fourth screw member from pulling out of the fourth internal screw guide.

19. The apparatus according to claim 18, wherein the first screw member and the fourth screw member are oriented rostrally (superiorly) and the second screw member and the third screw member are oriented caudally (inferiorly).

20. The apparatus according to claim 19, wherein the second screw member and the third screw member are disposed between the first screw member and the fourth screw member along a longitudinal length of the intervertebral cage.

21. The apparatus according to claim 1, wherein the first screw locking mechanism is disposed between the intervertebral cage and the underside of the screw head of the first screw member and/or the second screw member when the first screw locking mechanism is in an un-locked state.

22. The apparatus according to claim 1, wherein the threaded body of the first screw member and/or the second screw member engages the first screw locking mechanism.

23. The apparatus according to claim 1, wherein the threaded body of the first screw member and the second screw member engages the first screw locking mechanism.

24. The apparatus according to claim 22, wherein the threaded body of the first screw member and/or the second screw member mechanically indents the first screw locking mechanism when the first screw locking mechanism is in the locked state.

25. The apparatus according to claim 23, wherein the threaded body of the first screw member and the second screw member mechanically indents the first screw locking mechanism when the first screw locking mechanism is in the locked state.

26. The apparatus according to claim 1, wherein the first screw locking mechanism is reusable for a limited number of cycles.

27. The apparatus according to claim 23, wherein the intervertebral cage includes a surface having a first opening of the first internal screw guide and a second opening of the second internal screw guide,
   wherein the surface of the intervertebral cage includes a third opening formed between the first opening of the first internal screw guide and the second opening of the second internal screw guide, and
   wherein the first screw locking mechanism includes a projection that is received in the opening of the intervertebral cage when the first screw locking mechanism is secured to the intervertebral cage.

28. The apparatus according to claim 23, wherein the first screw locking mechanism comprises:
   a first curved portion that engages the threaded body of the first screw member;
   a second curved portion that engages the threaded body of the second screw member; and
   a central portion that connects the first curved portion to the second curved portion.

29. The apparatus according to claim 28, wherein the intervertebral cage includes a surface having a first opening of the first internal screw guide and a second opening of the second internal screw guide,
   wherein the surface of the intervertebral cage includes a third opening formed between the first opening of the first internal screw guide and the second opening of the second internal screw guide,
   wherein the first screw locking mechanism includes a projection extending from an underside of the central portion, and
   wherein the projection is received in the opening of the intervertebral cage when the first screw locking mechanism is secured to the intervertebral cage.

30. The apparatus according to claim 28, wherein the first curved portion is curved in a direction opposite to the second curved portion.

31. The apparatus according to claim 1, wherein each of the first internal screw guide and the second internal screw guide has a 25 degree angulation.

32. The apparatus according to claim 31, wherein each of the first internal screw guide and the second internal screw guide is angled to orient the first screw member and the second screw bi-directionally in opposite directions.

33. The apparatus according to claim 31, wherein each of the first internal screw guide and the second internal screw guide includes a tunnel that permits only the 25 degree angulation of the first screw member and the second screw member.

34. The apparatus according to claim 1, wherein a surface of each longitudinal end of the intervertebral cage includes a slot formed adjacent to an edge of an upper surface of the intervertebral cage.

35. The apparatus according to claim 1, wherein a surface of each longitudinal end of the intervertebral cage includes an edge having an elliptical contour.

36. A bi-directional fixating transvertebral (BDFT) screw/cage apparatus, comprising:
   an intervertebral cage for maintaining disc height, the intervertebral cage including a first internal screw guide, a second internal screw guide, a third internal screw guide, and a fourth internal screw guide, each having a predetermined angled trajectory;
   a first screw member, a second screw member, a third screw member, and a fourth screw member, each having a screw head, a tapered end, and a threaded body disposed within the intervertebral cage; and
   a screw locking mechanism that prevents the first screw member, the second screw member, the third screw member, and/or the fourth screw from pulling-out of the first internal screw guide, the second internal screw guide, the third internal screw guide, and/or the fourth internal screw guide respectively,
   wherein the screw locking mechanism is disposed between the intervertebral cage and an underside of the screw head of each of the first screw member, the second screw member, the third screw member, and/or the fourth screw member when the screw locking mechanism is in a locked state.

37. The apparatus according to claim 36, wherein the first internal screw guide, the second internal screw guide, the third internal screw guide, and/or the fourth internal screw guide are aligned along a longitudinal axis of the intervertebral cage.

38. The apparatus according to claim 36, wherein the first internal screw guide, the second internal screw guide, the third internal screw guide, and the fourth internal screw guide are symmetrically disposed on each side of a center point of the intervertebral cage along a longitudinal axis of the intervertebral cage.

39. The apparatus according to claim 36, wherein the first screw member and the fourth screw member are oriented rostrally (superiorly) and the second screw member and the third screw member are oriented caudally (inferiorly).

40. The apparatus according to claim 36, wherein the second screw member and the third screw member are disposed between the first screw member and the fourth screw member along a longitudinal axis of the intervertebral cage.

41. An integral intervertebral cage spacer and bi-directional fixating/fusion transvertebral body screw apparatus, comprising:
   an intervertebral cage including a plurality of internal angled screw guides;
   a plurality of screw members having a screw head, a tapered end, and a threaded body disposed within the plurality of internal angled screw guides of the intervertebral cage; and
   a screw locking mechanism that prevents the plurality of screw members from pulling out of the plurality of internal angled screw guides,
   wherein the plurality of internal angled screw guides orients a first screw member of the plurality of screw members rostrally (superiorly) and a second screw member of the plurality of screw members caudally (inferiorly),
   wherein the screw locking mechanism is disposed between the intervertebral cage and an underside of the screw head of each of the plurality of screw members when the screw locking mechanism is in a locked state.

42. A method of inserting a bi-directional fixating transvertebral (BDFT) screw/cage apparatus between a first vertebral body and a second vertebral body, the method comprising:
   measuring a dimension of a disc space between the first vertebral body and the second vertebral body;
   determining that the disc space is a posterior lumbar disc space, an anterior lumbar disc space, or an anterior cervical disc space;

selecting an intervertebral cage based on the measured dimension of the disc space and based on the determination of the disc space being the posterior lumbar disc space, the anterior lumbar disc space, or the anterior cervical disc space;

inserting the selected intervertebral cage into a midline of the disc space until the selected intervertebral cage is flush or countersunk relative to the first vertebral body and the second vertebral body;

inserting a first screw member, having a screw head, a tapered end, and a threaded body, into a first internal screw guide of the selected intervertebral cage;

inserting a second screw member, having a screw head, a tapered end, and a threaded body, into a second internal screw guide of the selected intervertebral cage;

screwing the first screw member and the second screw member into the first vertebral body and the second vertebral body respectively;

confirming a position and placement of the intervertebral cage relative to the first vertebral body and the second vertebral body; and locking the first screw member and the second screw member in a final position by embedding a portion of the threaded body of the first screw member and the second screw member into a screw locking mechanism of the selected intervertebral cage, wherein the screw locking mechanism is disposed between the intervertebral cage and an underside of the screw head of the first screw member and the second screw member when the first screw member and the second screw member are in a locked state.

* * * * *